(12) United States Patent
Shirtliff et al.

(10) Patent No.: US 9,265,820 B2
(45) Date of Patent: Feb. 23, 2016

(54) **MULTIVALENT VACCINE PROTECTION FROM *STAPHYLOCOCCUS AUREUS* INFECTION**

(71) Applicant: UNIVERSITY OF MARYLAND, BALTIMORE, Baltimore, MD (US)

(72) Inventors: Mark Shirtliff, Ellicott City, MD (US); Janette Harro, York, PA (US); Jeffrey Leid, Flagstaff, AZ (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/382,837

(22) PCT Filed: Mar. 5, 2013

(86) PCT No.: PCT/US2013/029053
§ 371 (c)(1),
(2) Date: Sep. 4, 2014

(87) PCT Pub. No.: WO2013/134225
PCT Pub. Date: Sep. 12, 2013

(65) Prior Publication Data
US 2015/0024000 A1    Jan. 22, 2015

Related U.S. Application Data

(60) Provisional application No. 61/606,750, filed on Mar. 5, 2012.

(51) Int. Cl.
*A61K 39/295* (2006.01)
*A61K 39/085* (2006.01)
*A61K 39/116* (2006.01)
*A61K 39/09* (2006.01)
*A61K 38/14* (2006.01)
*A61K 39/00* (2006.01)

(52) U.S. Cl.
CPC ............... *A61K 39/092* (2013.01); *A61K 38/14* (2013.01); *A61K 39/085* (2013.01); *A61K 2039/70* (2013.01)

(58) Field of Classification Search
None
See application file for complete search history.

(56) References Cited

U.S. PATENT DOCUMENTS

| | | | |
|---|---|---|---|
| 7,608,276 | B2 | 10/2009 | Masignani et al. |
| 2006/0234233 | A1 | 10/2006 | Bruce et al. |
| 2010/0285496 | A1 | 11/2010 | Leid et al. |
| 2011/0177111 | A1 | 7/2011 | Shirtliff et al. |

OTHER PUBLICATIONS

Brady et al. Infect. Immun. 74: 3415-3426, 2006.*
Prabhakara et al. Infect. Immun. 79: 1789-1796, Jan. 31, 2011.*
Greenspan et al. Nature Biotechnology 17: 936-937, 1999.*
Skolnick et al. Trends in Biotechnology, 18: 34-39, 2000.*
Brady, R. et al., Resolution of *Staphylococcus aureus* Biofilm Infection Using Vaccination and Antibiotic Treatment, Infection and Immunity, 2011, vol. 79, No. 4, pp. 1797-1803.
International Search Report for PCT/US2013/029053, dated Jun. 21, 2013.

* cited by examiner

*Primary Examiner* — S. Devi
(74) *Attorney, Agent, or Firm* — Wenderoth, Lind & Ponack, L.L.P.

(57) ABSTRACT

Vaccine formulations effective against *Staphylococcus aureus*, including methicillin-resistant *Staphylococcus aureus* (MRSA) are disclosed, as well as methods of using the vaccine formulations in the treatment and prevention of *Staphylococcus aureus* infections in a subject.

8 Claims, 3 Drawing Sheets

MULTIVALENT VACCINE PROTECTION FROM *STAPHYLOCOCCUS AUREUS* INFECTION

STATEMENT OF GOVERNMENTAL INTEREST

This invention was made with government support under Grant Number AI069568 awarded by the National Institutes of Health. The government has certain rights in the invention.

BACKGROUND

1. Field of the Invention

The present invention relates to multivalent vaccine formulations effective against *Staphylococcus aureus*, including both biofilm and planktonic types of bacterial infections, and to methods of using the formulations in the treatment and prevention of *S. aureus* infections in subjects.

2. Related Art

One of the most common and costly problems for the U.S. healthcare system is nosocomial infections (26), with *S. aureus* being the second-leading cause of such infections (4). Methicillin-resistant *S. aureus* (MRSA) is responsible for 40-60% of all nosocomially-acquired *S. aureus* infections, and these resistant strains are now considered to be endemic in the hospital setting (36). Community-associated *S. aureus* strains may also acquire methicillin-resistance (CA-MRSA) and the modern emergence of such strains is of great concern (24, 31, 64).

Recent studies indicate that *S. aureus* is also the major mediator of prosthetic implant infection (1, 54). The increasing involvement of *S. aureus* in foreign body-related infections, the rapid development of resistance to multiple antibiotics by these organisms, and the propensity of these infections to change from an acute infection to one that is persistent, chronic and recurrent have led to this organism once again receiving significant attention.

Treating prosthetic implant infections is a complicated process, and a number of staphylococcal defense mechanisms may be responsible for this difficulty as well as the capacity of *S. aureus* to evade clearance by the host immune response. One of the most important mechanisms utilized by *S. aureus* to thwart the host immune response and develop into a persistent infection is through the formation of a highly-developed biofilm. A biofilm is defined as a microbe-derived community in which bacterial cells are attached to a hydrated surface and embedded in a polysaccharide matrix (13). Bacteria in a biofilm exhibit an altered phenotype in their growth, gene expression, and protein production (17), and prosthetic medical devices are often a site of chronic infection, because they present a suitable substrate for bacterial adherence, colonization, and biofilm formation. Biofilm formation by *S. aureus* during prosthetic implant infection makes eradication of this bacteria extremely difficult, due in part to the dramatically increased resistance of bacteria in a biofilm to host defenses (21) and to antibiotics (46, 51), compared to their planktonic counterparts.

Previous vaccine studies have evaluated the efficacy of bacterial polysaccharides, e.g. polysaccharide capsules, exopolysaccharide, and peptidoglycan (10, 20, 38, 41), as well as recombinant protein subunit vaccines (2, 8, 9, 27, 29, 30, 33, 57, 65) against *S. aureus* infection, but none have demonstrated complete eradication of *S. aureus* in experimental animal models (2, 8, 9, 27, 29, 30, 33, 57, 65) or passed the rigors of phase III clinical testing (56, 59). Most vaccines evaluated to date do not account for biological redundancy of *S. aureus* virulence factors, differential protein expression during different modes of growth (exponential growth versus stationary) or type of infection (planktonic versus biofilm), and the lack of antigen conservation amongst relevant clinical isolates. Indeed, a polysaccharide vaccine (StaphVAX) developed using the *S. aureus* capsular polysaccharide 5 (CP5) and capsular polysaccharide 8 (CP8) conjugated to the *Pseudomonas aeruginosa* exotoxoid A failed to provide protection in phase III clinical trials against *S. aureus*-mediated bacteremia in two different cohorts of 1804 and 3600 hemodialysis patients (59). Factors contributing to this failure are the existence of non-encapsulated strains (CP5 and CP8 strains account for 75-80% of isolates) (12) and differential expression as extrapolated from in vitro data indicating that capsular polysaccharide expression is limited to the stationary mode of growth and the absence of CP5 expression in *S. aureus* bound to endothelial cells (48). The efficacy of the StaphVAX vaccine would, therefore, be limited to planktonic-type infections and ineffective at targeting the humoral response to a *S. aureus* biofilm.

Similar to the findings with the CP5/CP8 vaccine (20), subunit vaccines developed against the clumping factor A (ClfA) (2, 27), clumping factor B (ClfB) (57), fibronectin binding protein (FnBP) (65), α-Hemolysin (9, 29), Panton-Valentine leukocidin (PVL) (8), and the iron-regulated surface determinant B (IsdB) (30, 33) mediate partial protection in experimental animal models. These subunit vaccines did not provide complete protection, despite the candidate proteins being highly immunogenic in vivo (25, 33, 57) and the resultant antibodies promoting opsonic killing of *S. aureus* (65). One deficiency of these approaches was relying on a monovalent vaccine to promote protection against the pathogen. *S. aureus* has nearly 70 virulence factors and functional redundancy amongst these factors may abrogate the effect of neutralizing one factor. Arguably, *S. aureus* expresses multiple iron acquisition systems: siderophores staphyloferrin A and B transport transferrin to receptors HtsA and SirA (14, 43), an ABC transporter Fhu imports $Fe^{3+}$ hydroxamates (58), and iron-regulated surface determinant (Isd) B and IsdH receptors that bind hemoglobin/haptoglobin complexes (18, 62), therefore the overall effectiveness of anti-IsdB antibodies that block IsdB-mediated hemoglobin binding may be only a modest effect on iron uptake and the organism's pathogenicity (30). The validity of this argument is exemplified by the cessation of phase III clinical trials of Merck's IsdB vaccine (V710) that failed to provide complete protection (16), despite promising immunogenicity and opsonic killing data from phase II trials (25, 52).

Efficacy of a monovalent vaccine can also be compromised by differential expression of the targeted protein during the course of infection. While *S. aureus* initiates colonization by binding host extracellular ligands using its adhesin proteins called microbial surface components recognizing adhesive matrix molecules (MSCRAMMs), including the fibronectin-binding protein (FnBP), these factors are mostly down-regulated as the sessile bacteria encapsulate themselves in an extracellular polysaccharide matrix, or biofilm (44, 55). Hence, vaccines designed to target a MSCRAMM will be ineffective at clearance after the bacteria transition into the biofilm phenotype. Evaluation of the MSCRAMM FnBP vaccine demonstrated it provided partial protection against *S. aureus* in a murine model of sepsis, but the study failed to enumerate bacteria in the blood and/or kidneys to verify bacterial clearance. It is feasible that *S. aureus* can subvert the humoral response to FnBP, form a sessile biofilm and down-regulate FnBP, and become completely recalcitrant the host response.

A vaccine strategy that circumvents the incomplete protection of monovalent vaccines caused by protein redundancy, differential protein expression, or isolate-specific genetic divergence is the generation of a multifactorial assault using a multivalent subunit vaccine. Stranger-Jones et al. demonstrated a quadrivalent vaccine comprised of surface-exposed proteins: iron-regulated surface determinant A (IsdA), IsdB, and serine aspartate repeat protein D (SdrD), and SdrE increased survival rates against *S. aureus*-mediated lethal challenge compared to protection afforded by each monovalent variant (61). Although the authors stressed the survival rates after lethal challenge, they omitted enumeration of *S. aureus* in the kidneys and survival rates beyond 7 days post-infection from the data analysis. These omissions preclude a conclusion to be reached on the vaccine's ability to promote complete bacterial clearance and prevent future complications due to *S. aureus* persistence via biofilm formation. Overall, the multivalent vaccine had limited efficacy, providing complete protection against only two of five clinical *S. aureus* isolates tested (61). In addition, comparative analysis of multiple *S. aureus* genomes found a lack of conservation amongst some surface proteins, including SdrD and SdrE (39), which indicates the limited efficacy of the IsdA/IsdB/SdrD/SdrE vaccine formulation may extend beyond the clinical isolates tested by Stranger-Jones.

Vaccine studies have predominately focused on protection against planktonic-mediated infection by examining sepsis (20, 27, 33, 38, 41, 61, 65) or pneumonia (9), while few studies have incidentally evaluated protection, mediated by popular vaccine candidates, against biofilm infection with experimental endocarditis (2), skin (8, 22, 29), or abscess models (20, 61). As a departure from previous *S. aureus* vaccine strategies, Brady et al. focused on identifying biofilm upregulated proteins that are immunogenic (4) and established that a multivalent biofilm-based vaccine when coupled with vancomycin treatment could eradicate a biofilm infection, which is traditionally recalcitrant to clearance by either antibiotic treatment or immune response (5). Previous attempts to target the biofilm phenotype, most notably against the staphylococcal intercellular adhesion (PIA) composed of poly-N-acetyl-β-1,6-glucosamine (PNAG) (38, 40, 41), were directed towards the biofilm matrix encapsulating the bacteria versus cell wall-associated proteins. The polysaccharide PNAG vaccine elicited a response that reduced bacterial counts (40), but polysaccharides tend to be weak immunogens and induce antibodies with low opsonic killing activity. In addition, PNAG molecules tend to be loosely associated with the bacterial surface and the acetylated PNAG form is released into suspension (11). Efforts to improve efficacy of the PNAG vaccine have evaluated the deacetylated form of PNAG (dPNAG), which may be retained on the cell surface, conjugated to diphtheria toxoid or a synthetic 9-mer of β-(1→6)-D-glucosamine (GlcNH$_2$) conjugated to tetanus toxoid, but partial protection against multiple *S. aureus* strains was observed despite improved immunogenicity (22, 38). PIA is generated by enzymes encoded on the icaABDC locus (28), but the presence of the icaABDC locus does not directly correlate to biofilm formation in vitro (32) and the icaABDC locus in *S. aureus* was dispensable in a subset of in vivo orthopedic prosthesis-associated and catheter-associated infections, which are identified as biofilm-mediated infections (53). While the efficacy of the PNAG vaccine against *S. aureus* biofilms requires further evaluation, the dispensability of the icaABDC locus in some *S. aureus* strains isolated from clinical infections suggests that the PNAG vaccine would provide limited protection against *S. aureus* biofilm infections.

Another consideration for vaccine development is the type of response elicited by the host immune system and the ability of the pathogen to subvert immune mediators using immunoavoidance factors, which may have varied outcomes depending on the host environment. The immune response elicited in vitro against *S. aureus* or its virulence factors, specifically staphylococcal enterotoxin A or B and the alpha toxin, is a pro-inflammatory Th1-response (3, 7, 15, 42). Indeed, comparison of *S. aureus* bacteremia outcomes in mice with different genetic backgrounds found that Th1-biased C57BL/6J mice were resistant and Th2-biased BALB/c mice were susceptible to this acute form of *S. aureus* infection (63). In contrast, a robust Th-1 response was elicited against a *S. aureus* implant infection in C57BL/6J mice, but the mice were susceptible and developed a chronic infection with $10^7$ CFU/tibia at 49 days post-infection (45). The *S. aureus* biofilm appears to be recalcitrant to the pro-inflammatory response, which damages host tissue at the infection site generating devitalized sites for *S. aureus* to colonize. Subsequent evaluation found that Th-2 biased BALB/c mice were resistant to the *S. aureus* implant infection, and ablation of interleukin-4 or the depletion of Treg cells abrogated the protection against *S. aureus* in BALB/c mice (46). Th2-mediated resistance to bacterial infection was also revealed for subcutaneous infections with *S. aureus*, where higher bacterial loads were observed in C57BL/6J mice versus BALB/c mice (45). Increased CXCL-2 expression in the C57BL/6J mice correlated with the susceptibility to subcutaneous infection (45), and may halt the killing activity of polymorphonuclear neutrophils (PMNs) after influx and internalization of *S. aureus* (23). This differential immune response against *S. aureus*, which was observed with chronic infections (implant or subcutaneous) versus acute (sepsis), indicates that the choice of mouse strain may impact the outcome of vaccine studies. Most vaccine studies have examined protection against *S. aureus* using experimental models developed in BALB/c mice (2, 8, 33, 61, 65), while few studies have evaluated vaccine efficacy in C57BL/6J mice (9, 29). Emphasis on BALB/c experimental models to evaluate *S. aureus* vaccines may yield insight about efficacy against acute or planktonic infections, but these models will be poor evaluators of chronic, biofilm infections and do not represent the immune response bias in humans.

Additional vaccine formulations would add to the arsenal of means used to treat and/or prevent *S. aureus* infections.

SUMMARY

*Staphylococcus aureus* has re-emerged as a major human pathogen and there are presently no vaccines that afford consistent, long-term protection against *S. aureus* infections. While infections, particularly those with MRSA, are often nosocomial in origin, community acquired infections associated with this microbial species have reached epidemic levels. One of the ways in which *S. aureus* is able to persist in the host and remain recalcitrant to clearance by the immune system or antimicrobial agents is through a biofilm mode of growth. Therefore, an effective vaccine and/or treatment modality that could prevent the establishment of biofilm-mediated chronic infections by *S. aureus* is needed.

The present invention demonstrates protection against biofilm-associated *S. aureus* infection through the use of a multicomponent vaccine, alone or in combination with subsequent antimicrobial agent therapy. Complete protection was demonstrated in a murine tibial implant model using a biofilm- and planktonic-specific pentavalent vaccine, with 100% clearance of *S. aureus*.

The vaccine formulations of the present invention hold significant promise for those with identified risk factors for *S. aureus* biofilm infection. Even in patients that acquire a *S. aureus* infection, an anti-biofilm vaccine could allow these previously untreatable infections to be halted or cured without the need for surgical intervention. The present invention thus provides new means to limit and eradiate *S. aureus* biofilm infections that could help to prevent the onset of chronic disease, saving patients from significant morbidity and mortality.

The present invention is directed to the following embodiments of vaccine formulations.

In a first embodiment the present invention is directed to a vaccine formulation comprising five different polypeptides of a strain of *S. aureus* (a first, second, third, fourth and fifth polypeptide of a strain of *S. aureus*), or portions thereof, or variants thereof, or combinations thereof, and a pharmaceutically acceptable carrier or diluent. The strain of *S. aureus* may be a methicillin-resistant or a methicillin-sensitive strain of *S. aureus*.

In one aspect, at least one of the *S. aureus* polypeptides is a polypeptide expressed by a planktonic form of the bacteria and at least one of the *S. aureus* polypeptides is a polypeptide expressed by a biofilm form of the bacteria. In a related aspect, one of the *S. aureus* polypeptides is a polypeptide expressed by a planktonic form of the bacteria and four of the *S. aureus* polypeptides are polypeptides expressed by a biofilm form of the bacteria.

In another aspect, the first, second, third, fourth and fifth polypeptides are *S. aureus* polypeptide SA0037 set forth in SEQ ID NO:13, *S. aureus* polypeptide SA0119 set forth in SEQ ID NO:14, *S. aureus* polypeptide SA0486 set forth in SEQ ID NO:15, *S. aureus* polypeptide SA0688 set forth in SEQ ID NO:16, and *S. aureus* glucosaminidase set forth in SEQ ID NO:17.

In further aspects, the vaccine formulations comprise one or more portions of one or more of the *S. aureus* polypeptides, wherein the portions individually encompass at least about 20 contiguous amino acids of the full length polypeptide. In the same or aspects, the vaccine formulations comprise one or more variants of one or more of the *S. aureus* polypeptides or portions thereof, wherein the variants individually have at least about 95% identity to a *S. aureus* polypeptide or portion thereof.

In a particular aspect, the present invention is directed to a vaccine formulation comprising five different, full-length polypeptides of a strain of *S. aureus*. In one example, the five polypeptides are *S. aureus* polypeptide SA0037 set forth in SEQ ID NO:13, *S. aureus* polypeptide SA0119 set forth in SEQ ID NO:14, *S. aureus* polypeptide SA0486 set forth in SEQ ID NO:15, *S. aureus* polypeptide SA0688 set forth in SEQ ID NO:16, and *S. aureus* glucosaminidase set forth in SEQ ID NO:17.

The present invention is also directed to the following embodiments of methods of using the vaccine formulations of the invention. Thus, in a second embodiment, the present invention is directed to methods of generating an immune response in a subject comprising administering an immunologically effective amount of a vaccine formulation of the present invention to a subject, thereby generating an immune response in a subject. In one aspect, the immune response is a protective immune response.

In a third embodiment the present invention is directed to methods for treating a *S. aureus* infection in a subject, comprising administering a therapeutically effective amount of a vaccine formulation of the present invention to a subject having a *S. aureus* infection, thereby treating a *S. aureus* infection in a subject.

In a fourth embodiment the present invention is directed to methods of inhibiting a *S. aureus* infection in a subject, comprising administering a therapeutically effective amount of a vaccine formulation of the present invention to a subject at risk of developing a *S. aureus* infection, thereby inhibiting a *S. aureus* infection in a subject.

In related embodiments, the methods for treating or inhibiting a *S. aureus* infection may further comprise administering one or more antimicrobial agents to a subject having a *S. aureus* infection or at risk of developing a *S. aureus* infection, wherein the antimicrobial agent is administered prior to, concurrent with or after the vaccine formulation. In these embodiments the antimicrobial agent(s) may be selected from the group that includes, but is not limited to, an Aminoglycoside, such as Amikacin, Gentamicin, Kanamycin, Neomycin, Netilmicin, Streptomycin, Tobramycin or Paromomycin; a Carbacephem, such as Loracarbef; a Carbapenem, such as Ertapenem, Doripenem, Imipenem/Cilastatin or Meropenem; a Cephalosporin, such as Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime or Ceftobiprole; a Glycopeptide, such as Teicoplanin or Vancomycin; a Macrolide, such as Azithromycin, Clarithromycin, Dirithromycin, Erythromycin, Erythroped, Roxithromycin, Troleandomycin, Telithromycin or Spectinomycin; a Monobactam, such as Aztreonam; a Penicillin, such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin or Ticarcillin; a Polypeptide, such as Bacitracin, Colistin or Polymyxin B; a Quinolone, such as Ciprofloxacin, Enoxacin, Gatifloxacin, Levofloxacin, Lomefloxacin, Moxifloxacin, Norfloxacin, Ofloxacin or Trovafloxacin; a Sulfonamide, such as Mafenide, Prontosil (archaic), Sulfacetamide, Sulfamethizole, Sulfanilamide (archaic), Sulfasalazine, Sulfisoxazole, Trimethoprim or Trimethoprim-Sulfamethoxazole (Cotrimoxazole) (TMP-SMX); a Tetracycline, such as Demeclocycline, Doxycycline, Minocycline, Oxytetracycline or Tetracycline; as well as Chloramphenicol, Clindamycin, Lincomycin, Fusidic acid, Furazolidone, Linezolid, Metronidazole, Mupirocin, Nitrofurantoin, Macrobid, Platensimycin, Quinupristin/Dalfopristin, Rifampin or Rifampicin.

In the embodiments directed to methods of treatment and inhibition, the *S. aureus* infection may be any *S. aureus* infection of a subject, including, for example, one or more of a *S. aureus* biofilm infection, a planktonic *S. aureus* infection, a *S. aureus* osteomyelitis infection, a biofilm-associated *S. aureus* osteomyelitis infection, a *S. aureus* indwelling medical device infection, a *S. aureus* endocarditis infection, a *S. aureus* diabetic wound or ulcer infection, a *S. aureus* chronic rhinosinusitis infection, a *S. aureus* ventilator associated pneumonia infection, a *S. aureus* intravenous catheter associated infection, a *S. aureus* skin infection, a *S. aureus* necrotizing fasciitis, a *S. aureus* keratitis, a *S. aureus* endophthlamitis, a *S. aureus* pyopneumothorax, a *S. aureus* empyema, and a *S. aureus* septicemia.

DETAILED DESCRIPTION

Figure 1:
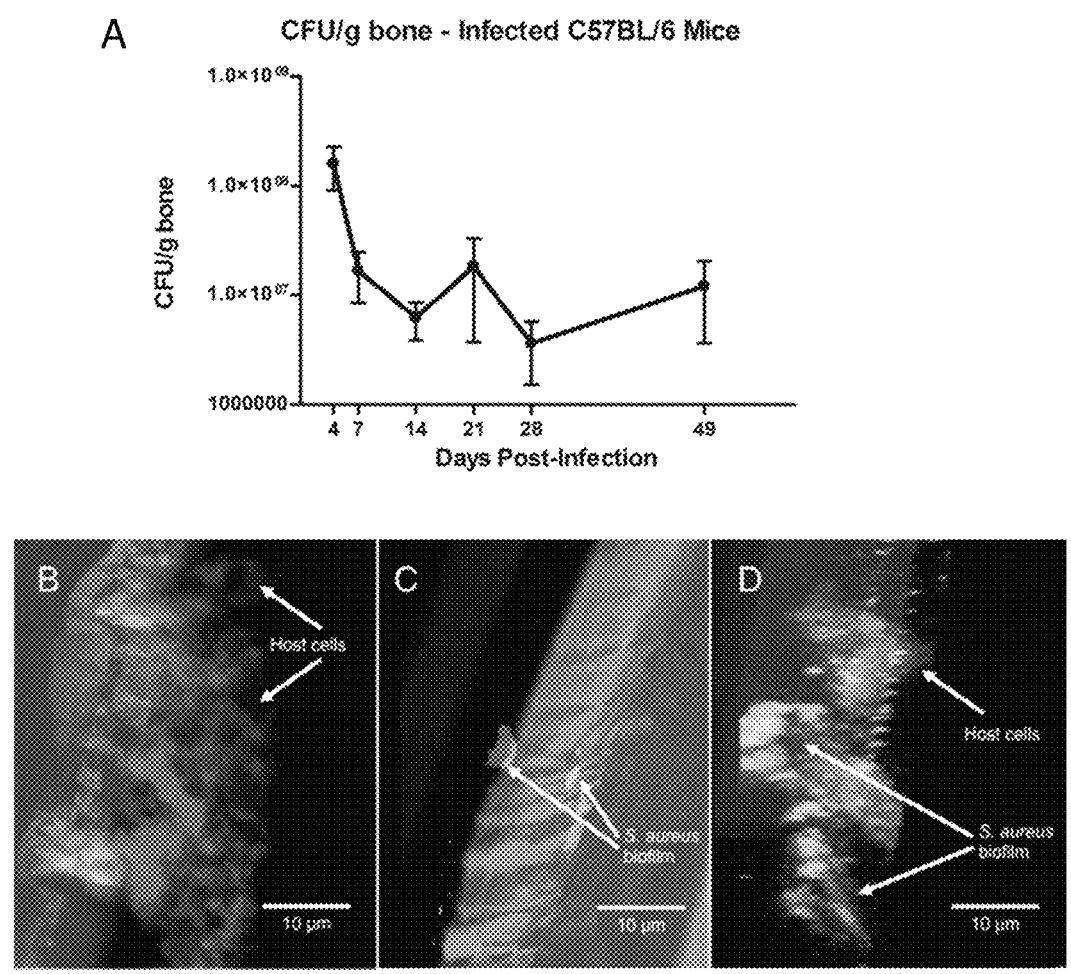
FIG. 1: (A) Development of chronic, biofilm-mediated infection that is recalcitrant to antimicrobial therapy. CFU/g bone over time, indicating the development of a chronic infection. Tibiae from infected and uninfected mice were removed at days 4, 7, 14, 21, 28, and 49 days post-infection. No CFUs were found in uninfected mice. Serial dilutions of bone homogenates were plated on blood agar plates. CFU/g bone were calculated and plotted over time (n=5-8 mice per group, experiments performed in triplicate, * denotes p<0.05 compared to controls by Fishers exact test). Bars represent SD. (B-D) Confocal scanning laser microscopic images of (B) uninfected pins removed 21 days post-implantation, and S. aureus infected pins removed at (C) 7 and (D) 21 days post-implantation. Pins were labeled using a FITC-labeled PNA-FISH probe. Biofilm formation is evident on the pin removed from the infected mouse.

Biofilm-embedded bacteria have remarkably different phenotypic and antigenic properties compared to their free-floating, planktonic counterparts. These differences have presented a struggle when designing vaccine formulations for use in treating and preventing both types of bacterial infections. Even individual stages of biofilm growth (from early attached to maturing and fully mature stages) have been shown to be more antigenically distinct from one another than even biofilm versus planktonic bacteria (66).

Through extensive research into acceptable vaccine candidates, the inventors have identified genes expressed/produced uniquely in biofilm and in planktonic modes of growth via proteomics and transcriptomics techniques. In particular, the inventors found that one must compare multiple stages of biofilm growth (from early attached to maturing and fully mature stages) to multiple stages of planktonic growth (early log, late log, stationary, and post stationary) in order to find those cell wall antigens with up-regulated and sustained expression in all biofilm stages and those with up-regulated and sustained expression in all planktonic growth stages. By combining biofilm and planktonic antigens that are expressed on the membrane or cell wall into a multivalent vaccine, protection of the host against microbial challenge by the specific microbial species can be elicited. This protection can be promoted since bacteria in the host exist in antigenically distinct forms of the planktonic and biofilm modes of growth during an infection and, as a result, a dual immune response against both phenotypes must be produced in the host.

The vaccine formulations of the present invention include antigens effective at priming the host immune response to clear both detached, free-floating populations of bacteria as well as bacteria forming a biofilm type of infection. This work is the first to acknowledge, and overcome, the differences of protein expression within different types of infection caused by the same microorganism, and demonstrate (as shown in the Examples) complete clearance in an S. aureus animal model of infection instead of only a significant reduction in bacterial populations.

As discussed above and herein, the present invention relates to vaccine formulations effective against S. aureus, including methicillin-resistant S. aureus (MRSA) and methicillin-sensitive S. aureus (MSSA), and to methods of using the vaccines in the treatment and prevention of S. aureus infections in a subject.

I. Vaccine Components—Proteins

The vaccine formulations of the present invention comprise at least a portion of each of five different polypeptides of a strain of S. aureus and a pharmaceutically acceptable carrier or diluent. The vaccine formulations are characterized in that they comprise at least one S. aureus polypeptide expressed by a planktonic form of the bacteria and at least one S. aureus polypeptide expressed by a biofilm form of the bacteria. The vaccine formulations of the present invention may thus comprise one, two, three, or four S. aureus polypeptides expressed by a planktonic form of the bacteria, and one, two, three, or four S. aureus polypeptides expressed by a biofilm form of the bacteria. In one aspect, the vaccine formulations comprise one S. aureus polypeptide expressed by a planktonic form of the bacteria and four S. aureus polypeptides expressed by a biofilm form of the bacteria.

The skilled artisan will understand that the identity, number and size of the different S. aureus proteins that can be included in the vaccine formulations of the present invention may vary. For example, the formulations may comprise only full-length versions of the polypeptides. Or the formulations may comprise only portions of the full-length polypeptides. Or the formulations may comprise a combination of portions and full-length polypeptides. Furthermore, combinations include formulations having one, two, three, four, five, six or more different portions of the same S. aureus polypeptide in combination with one or more portions of other polypeptides and/or full-length polypeptides and/or both portions and full-length versions of the same polypeptide. However, each of the formulations comprises at least one portion of each of five different polypeptides of a strain of S. aureus.

The identity of the planktonic- and biofilm-expressed polypeptides included in the vaccine formulations of the present invention is not particularly limited but each is a polypeptide from a strain of S. aureus. However, because the primary purpose of the vaccine formulations is to prime and activate the immune system of the subject receiving the vaccine formulation, the use of polypeptides exposed on the surface of the bacteria is particularly preferred. For example, the polypeptides may be cell wall and cell wall-associated polypeptides of S. aureus. Examples of such polypeptides include the S. aureus polypeptides SA0037 (SEQ ID NO:13), SA0119 (SEQ ID NO:14), SA0486 (SEQ ID NO:15), SA0688 (SEQ ID NO:16), and glucosaminidase (SEQ ID NO:17).

Additional S. aureus polypeptides that may be used in the vaccine formulations of the present invention include the polypeptides of Table 1.

TABLE 1

| Biofilm Expressed Polypeptides | |
|---|---|
| SACOL0405 | MATE efflux family protein (SEQ ID NO: 18) |
| SACOL0379 | bacteriophage L54a, M23/M37 peptidase domain protein (SEQ ID NO: 19) |
| SACOL2658 | arginine repressor (SEQ ID NO: 20) |
| SACOL1041 | hypothetical protein (SEQ ID NO: 21) |

TABLE 1-continued

| | |
|---|---|
| SACOL0048 | conserved hypothetical protein (SEQ ID NO: 22) |
| SACOL2292 | Na+/H+ antiporter (SEQ ID NO: 23) |
| SACOL0204 | formate acetyltransferase (SEQ ID NO: 24) |
| SACOL2729 | integrase/recombinase, core domain family (SEQ ID NO: 25) |
| SACOL2424 | 6-carboxyhexanoate--CoA ligase (SEQ ID NO: 26) |
| SACOL1183 | membrane protein, putative (SEQ ID NO: 27) |
| SACOL2446 | epimerase/dehydratase, putative (SEQ ID NO: 28) |
| SACOL0386 | bacteriophage L54a, hypothetical protein (SEQ ID NO: 29) |
| Planktonic Expressed Polypeptides | |
| SACOL0633 | conserved hypothetical protein (SEQ ID NO: 30) |
| SACOL1664 | conserved hypothetical protein TIGR00370 (SEQ ID NO: 31) |
| SACOL0541 | stage V sporulation protein G spoVG (SEQ ID NO: 32) |
| SACOL1138 | 29-kDa cell surface protein, putative sasJ (SEQ ID NO: 33) |
| SACOL0117 | polysaccharide extrusion protein (SEQ ID NO: 34) |
| SACOL1659 | conserved hypothetical protein (SEQ ID NO: 35) |
| SACOL2150 | mrp protein sasB (SEQ ID NO: 36) |

When only a portion(s) of a polypeptide is used in a vaccine formulation, the size of the peptide is only limited by its ability to be recognized by the immune system of the subject to which the vaccine is administered. In general, the peptides included in the formulations should be about 4, 5, 6, 7, 8, 9, 10, 11, 12, 13, 14, 15, 16, 17, 18, 19, 20, 21, 22, 23, 24, 25 or more contiguous amino acids of the full-length protein. The preferred size of the peptides is between about 20 amino acids and 3000 amino acids in length, more preferably between about 40 amino acids and 1500 amino acids in length, even more preferably between about 150 amino acids and 1300 amino acids in length. In other aspects, the peptides may 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99% of the size of the full-length protein.

As indicated above, the polypeptides and portions thereof used in the formulations of the present invention are from strains of *S. aureus*. There is no limitation on the different strains of *S. aureus* that might be used. As an example only, polypeptides from medically important strains of *S. aureus*, such methicillin-resistant *S. aureus* (either community-associated or hospital-acquired strains) and methicillin-sensitive *S. aureus*, may be used to constitute the vaccine formulations of the present invention. Therefore, the vaccine formulations of the present invention include the use of variants of the *S. aureus* polypeptides and portions thereof defined herein and having at least about 70%, 75%, 80%, 85%, 90%, 91%, 92%, 93%, 94%, 95%, 96%, 97%, 98% or 99% sequence identity over their entire length to *S. aureus* polypeptides and portions thereof. Sequence identity is determined by aligning the amino acid sequence of two peptides or proteins and calculating the number of amino acid differences over the entire length of the alignment. The skilled artisan will understand that there are a number of commercially available sequence manipulation programs for use in making such calculations, including the website of the National Center for Biotechnology Information.

The polypeptides, portions, and variants thereof (collectively, termed "proteins") used in the vaccine formulations may be obtained through any of the many well-established means known in the art. The skilled artisan will understand that the proteins can possess the native glycosylation of polypeptide as it is produced by the corresponding strain of *S. aureus*, or they can lack such glycosylation, or they can have altered glycosylation.

II. Vaccine Components—Carriers and Excipients

The pharmaceutically acceptable carrier, diluent or excipient included in the vaccine formulations will vary based on the identity of the proteins in the formulation, the means used to administer the formulation, the site of administration and the dosing schedule used. Suitable examples of carriers and diluents are well known to those skilled in the art and include water-for-injection, saline, buffered saline, dextrose, water, glycerol, ethanol, propylene glycol, polysorbate 80 (Tween-80™), poly(ethylene)glycol 300 and 400 (PEG 300 and 400), PEGylated castor oil (e.g. Cremophor EL), poloxamer 407 and 188, hydrophilic and hydrophobic carriers, and combinations thereof. Hydrophobic carriers include, for example, fat emulsions, lipids, PEGylated phospholipids, polymer matrices, biocompatible polymers, lipospheres, vesicles, particles, and liposomes. The terms specifically exclude cell culture medium. Additional carriers include cornstarch, gelatin, lactose, sucrose, microcrystalline cellulose, kaolin, mannitol, dicalcium phosphate, sodium chloride, alginic acid, croscarmellose sodium, and sodium starch glycolate.

Excipients included in a formulation have different purposes depending, for example on the nature of the vaccine formulation and the mode of administration. Examples of generally used excipients include, without limitation: stabilizing agents, solubilizing agents and surfactants, buffers, antioxidants and preservatives, tonicity agents, bulking agents, lubricating agents, emulsifiers, suspending or viscosity agents, inert diluents, fillers, disintegrating agents, binding agents, wetting agents, lubricating agents, antibacterials, chelating agents, sweetners, perfuming agents, flavouring agents, coloring agents, administration aids, and combinations thereof.

As a specific example, intramuscular preparations can be prepared and administered in a pharmaceutically acceptable diluent such as Water-for-Injection, 0.9% saline, or 5% glucose solution.

In one embodiment of the present invention, the vaccine formulations exist as atomized dispersions for delivery by inhalation. The atomized dispersion of the vaccine formulation typically contains carriers common for atomized or aerosolized dispersions, such as buffered saline and/or other compounds well known to those of skill in the art. The delivery of the vaccine formulations via inhalation has the effect of rapidly dispersing the vaccine formulation to a large area of mucosal tissues as well as quick absorption by the blood for circulation. One example of a method of preparing an atomized dispersion is described in U.S. Pat. No. 6,187,344, entitled, "Powdered Pharmaceutical Formulations Having Improved Dispersibility," which is hereby incorporated by reference in its entirety.

Additionally, the vaccines and vaccine formulations may also be administered in a liquid form. The liquid can be for oral dosage, for ophthalmic or nasal dosage as drops, or for use as an enema or douche. When the vaccine formulation is formulated as a liquid, the liquid can be either a solution or a suspension of the vaccine formulation. There are a variety of suitable formulations for the solution or suspension of the vaccine formulation that are well know to those of skill in the art, depending on the intended use thereof. Liquid formulations for oral administration prepared in water or other aqueous vehicles may contain various suspending agents such as methylcellulose, alginates, tragacanth, pectin, kelgin, carrageenan, *acacia*, polyvinylpyrrolidone, and polyvinyl alcohol. The liquid formulations may also include solutions, emulsions, syrups and elixirs containing, together with the active compound(s), wetting agents, sweeteners, and coloring and flavoring agents. Various liquid and powder formulations can be prepared by conventional methods for inhalation into the lungs of the mammal to be treated.

The vaccine formulations of the present invention may also include an adjuvant. Suitable adjuvants include Freund's Complete and Incomplete Adjuvant, Titermax, Oil in Water Adjuvants, as well as Aluminum compounds where antigens, normally proteins, are physically precipitated with hydrated insoluble salts of aluminum hydroxide or aluminum phosphate. Other adjuvants include liposome-type adjuvants comprising spheres having phospholipid bilayers that form an aqueous compartment containing the vaccine candidate and protecting it from rapid degradation, and that provide a depot effect for sustained release. Surface active agents may also be used as adjuvants and include lipoteichoic acid of gram-positive organisms, lipid A, and TDM. Quil A and QS-21 (saponin-type adjuvants), monophosphoryl lipid A, and lipophilic MDP derivatives are suitable adjuvants that have hydrophilic and hydrophobic domains from which their surface-active properties arise. Compounds normally found in the body such as vitamin A and E, and lysolecithin may also be used as surface-active agents. Other classes of adjuvants include glycan analog, coenzyme Q, amphotericin B, dimethyldioctadecylammonium bromide (DDA), levamisole, and benzimidazole compounds. The immunostimulation provided by a surface active agent may also be accomplished by either developing a fusion protein with non-active portions of the cholera toxin, exotoxin A, or the heat labile toxin from *E. coli* Immunomodulation through the use of anti-IL-17, anti IFN-γ, anti-IL-12, IL-2, IL-10, or IL-4 may also be used to promote a strong Th2 or antibody mediated response to the vaccine formulation.

III. Methods of Generating an Immune Response

The present invention is also directed to methods of generating an immune response in a subject to a vaccine formulation of the present invention. In one embodiment, the present invention is directed to methods of generating an immune response in a subject, comprising administering an immunologically effective amount of a vaccine formulation of the present invention to a subject, thereby generating an immune response in a subject. In each of the methods of generating an immune response of the present invention, the immune response is preferably a protective immune response.

An "immunologically effective amount" of a vaccine formulation is one that is sufficient to induce an immune response to vaccine components in the subject to which the vaccine formulation is administered. A "protective immune response" is one that confers on the subject to which the vaccine formulation is administered protective immunity against *S. aureus*. The protective immunity may be partial or complete immunity.

IV. Methods of Treatment and Prevention

The present invention is also directed to methods of treating a *S. aureus* infection in a subject using the vaccine formulations of the present invention. In one embodiment, the present invention is directed to methods of treating a *S. aureus* infection in a subject, comprising administering a therapeutically effective amount of a vaccine formulation of the present invention to a subject having a *S. aureus* infection, thereby treating a *S. aureus* infection in a subject. In certain aspects, the method further comprises administering an antimicrobial agent to the subject having a *S. aureus* infection in conjunction with the administration of the vaccine formulation.

The vaccine formulations of the present invention may also be used in methods of inhibiting a *S. aureus* infection in a subject. Such methods comprise administering a therapeutically effective amount of a vaccine formulation of the present invention to a subject at risk of developing a *S. aureus* infection, thereby inhibiting a *S. aureus* infection in a subject. In certain aspects, the method further comprises administering an antimicrobial agent to the subject at risk of developing a *S. aureus* infection in conjunction with the administration of the vaccine formulation.

A "therapeutically effective amount" of a vaccine formulation is one that is sufficient to provide at least some reduction in the symptoms of a *S. aureus* infection in a subject to which the vaccine formulation is administered, or one that is sufficient to achieve the goal of the method.

As used herein, the terms "treating" and "treatment" have their ordinary and customary meanings, and include one or more of, ameliorating a symptom of a *S. aureus* infection in a subject, blocking or ameliorating a recurrence of a symptom of a *S. aureus* infection in a subject, decreasing in severity and/or frequency a symptom of a *S. aureus* infection in a subject, as stasis, decreasing, or inhibiting growth of *S. aureus* in a subject. Treatment means ameliorating, blocking, reducing, decreasing or inhibiting by about 1% to about 100% versus a subject to which the vaccine formulation of the present invention has not been administered (with or without the additional administration of the antimicrobial agent). Preferably, the ameliorating, blocking, reducing, decreasing or inhibiting is 100%, 99%, 98%, 97%, 96%, 95%, 90%, 80%, 70%, 60%, 50%, 40%, 30%, 20%, 10%, 5% or 1%. The treatment may begin prior to, concurrent with, or after the onset of clinical symptoms of the infection. The results of the treatment may be permanent, such as where the *S. aureus* infection is completely cleared from the subject, or may be for a period of days (such as 1, 2, 3, 4, 5, 6 or 7 days), weeks (such as 1, 2, 3 or 4 weeks) or months (such as 1, 2, 3, 4, 5, 6 or more months).

As used herein, the terms "inhibit", "inhibiting" and "inhibition" have their ordinary and customary meanings, and include one or more of inhibiting colonization of *S. aureus*, inhibiting growth of *S. aureus* (all forms, including planktonic and biofilm) and inhibiting propagation of *S. aureus*. Such inhibition is an inhibition of about 1% to about 100% versus a subject to which the vaccine formulation of the present invention has not been administered (with or without the additional administration of the antimicrobial agent). Preferably, the inhibition is an inhibition of 100%, 99%, 98%, 97%, 96%, 95%, 90%, 80%, 70%, 60%, 50%, 40%, 30%, 20%, 10%, 5% or 1%. As used herein, the inhibition lasts at least a period of days, weeks, months or years upon completing of the dosing schedule. Preferably the inhibition is for the lifespan of the subject.

The methods for treating or inhibiting a *S. aureus* infection may further comprise administering one or more antimicrobial agents to a subject having a *S. aureus* infection or at risk of developing a *S. aureus* infection. When an antimicrobial agent is included in the methods of the present invention, the antimicrobial agent may be administered prior to, concurrent with or after the vaccine formulation is administered to the subject. Where the antimicrobial agent is administered prior to or after the vaccine formulation, the period of time between when the antimicrobial agent and the vaccine formulation are administered may be a period of hours (such as 6, 12, 18 or 24 hours), days (such as 1, 2, 3, 4, 5, 6 or 7 days), weeks (such as 1, 2, 3 or 4 weeks) or months (such as 1, 2, 3, 4, 5, 6 or more months). The antimicrobial agent may be any that is effective in the treatment of a *S. aureus* infection and may include, but is not limited to, an Aminoglycoside, such as Amikacin, Gentamicin, Kanamycin, Neomycin, Netilmicin, Streptomycin, Tobramycin or Paromomycin; a Carbacephem, such as Loracarbef; a Carbapenem, such as Ertapenem, Doripenem, Imipenem/Cilastatin or Meropenem; a Cephalosporin, such as Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime or Ceftobiprole; a Glycopeptide, such as Teicoplanin or Vancomycin; a Macrolide, such as Azithromycin, Clarithromycin, Dirithromycin, Erythromycin, Erythroped, Roxithromycin, Troleandomycin, Telithromycin or Spectinomycin; a Monobactam, such as Aztreonam; a Penicillin, such as Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin or Ticarcillin; a Polypeptide, such as Bacitracin, Colistin or Polymyxin B; a Quinolone, such as Ciprofloxacin, Enoxacin, Gatifloxacin, Levofloxacin, Lomefloxacin, Moxifloxacin, Norfloxacin, Ofloxacin or Trovafloxacin; a Sulfonamide, such as Mafenide, Prontosil (archaic), Sulfacetamide, Sulfamethizole, Sulfanilamide (archaic), Sulfasalazine, Sulfisoxazole, Trimethoprim or Trimethoprim-Sulfamethoxazole (Cotrimoxazole) (TMP-SMX); a Tetracycline, such as Demeclocycline, Doxycycline, Minocycline, Oxytetracycline or Tetracycline; as well as Chloramphenicol, Clindamycin, Lincomycin, Fusidic acid, Furazolidone, Linezolid, Metronidazole, Mupirocin, Nitrofurantoin, Macrobid, Platensimycin, Quinupristin/Dalfopristin, Rifampin or Rifampicin.

In each of the methods of the present invention the vaccine formulations are administered in a pharmaceutically acceptable form and in substantially non-toxic quantities. The vaccine formulations may be administered to a subject using different dosing schedules, depending on the particular use to which the formulations are put (e.g., administration to the subject pre- or post-exposure to $S.\ aureus$), the age and size of the subject, and the general health of the subject, to name only a few factors to be considered. In general, the vaccine formulations may be administered once, or twice, three times, four times, five times, six times or more, over a dosing schedule. The timing between each dose in a dosing schedule may range between a few hours, six, 12, or 18 hours, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more days. The same quantity of protein in the formulation may be administered in each dose of the dosing schedule, or the amounts in each dose may vary. The identity of the particular peptides and polypeptides in the formulation may also vary or remain the same in each dose in a dosing schedule.

The amount of protein administered to a subject in a dose when the methods of the present invention are practiced will vary based on the particular methods being practiced (e.g., prevention versus treatment of a $S.\ aureus$ infection), the means and formulation of administration, the age and size of the subject, and the general health of the subject, to name only a few factors to be considered. In general, however, the amount of $S.\ aureus$ protein administered to a subject in a dose will be sufficient to induce or boost an immune response in a subject to the components of the vaccine. For example, the vaccines formulations may contain between about 1 to about 1000 ug of total $S.\ aureus$ protein per kg of body weight of the subject to which the dose of the vaccine formulation will be administered, more preferably between about 10 to about 200 ug, even more preferably between about 15 to about 100 ug.

Appropriate doses and dosing schedules can readily be determined by techniques well known to those of ordinary skill in the art without undue experimentation. Such a determination will be based, in part, on the tolerability and efficacy of a particular dose.

Administration of the vaccine formulations may be via any of the means commonly known in the art of vaccine delivery. Such routes include intravenous, intraperitoneal, intramuscular, subcutaneous and intradermal routes of administration, as well as nasal application, by inhalation, ophthalmically, orally, rectally, vaginally, or by any other mode that results in the vaccine formulation contacting mucosal tissues.

As used herein, the $S.\ aureus$ infection may be any $S.\ aureus$ infection of a subject, including, for example, one or more of a $S.\ aureus$ biofilm infection, a planktonic $S.\ aureus$ infection, a $S.\ aureus$ osteomyelitis infection, a biofilm-associated $S.\ aureus$ osteomyelitis infection, a $S.\ aureus$ indwelling medical device infection, a $S.\ aureus$ endocarditis infection, a $S.\ aureus$ diabetic wound or ulcer infection, a $S.\ aureus$ chronic rhinosinusitis infection, a $S.\ aureus$ ventilator associated pneumonia infection, a $S.\ aureus$ intravenous catheter associated infection, a $S.\ aureus$ skin infection, a $S.\ aureus$ nectrotizing fasciitis, a $S.\ aureus$ keratitis, a $S.\ aureus$ endophthlamitis, a $S.\ aureus$ pyopneumothorax, a $S.\ aureus$ empyema, and a $S.\ aureus$ septicemia.

The term "subject" is intended to mean an animal, such birds or mammals, including humans and animals of veterinary or agricultural importance, such as dogs, cats, horses, sheep, goats, and cattle.

A kit comprising the necessary components of a vaccine formulation that elicits an immune response to a strain of $S.\ aureus$ and instructions for its use is also within the purview of the present invention.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Materials and Methods

Unless stated otherwise, the following experimental details pertain to each of the examples provided in the specific Examples set forth and discussed below.

Mice. Inbred C57BL/6 (6-8 weeks old) were purchased from Jackson Laboratories (Bar Harbor, Me.). Mice were maintained under micro-isolator conditions in the animal facility at the University of Maryland Dental School (Baltimore, Md.), in accordance with protocols reviewed and approved by the Institutional Animal Care and Use Committee (IACUC).

Bacterial strain and preparation of infectious inocula. The strain of $S.\ aureus$ used in these experiments, MRSA-M2, is a clinical isolate obtained from an osteomyelitis patient undergoing treatment at the University of Texas Medical Branch (Galveston, Tex.) and has been used in previous biofilm molecular analyses and animal infection models (5, 34, 37, 60) (6, 47, 49, 50). An overnight $S.\ aureus$ Tryptic Soy Broth (TSB) culture grown at 37° C. with 250 rpm shaking was diluted 1:100 in fresh, prewarmed TSB and incubated for 2 h at 37° C. with 250 rpm shaking. Cells were centrifuged, rinsed with PBS, counted via a Petroff Hausser counter, and diluted to $1\times10^6$ CFU/ml.

Cloning, expression, and purification of proteins. Candidate antigens selected from Brady et al. (5) were amplified using the primers listed in Table 2.

TABLE 2

Primers utilized in this study
(all products amplified from *S. aureus* M2 MRSA strain).

| Primer name | Sequence (5'-3'); SEQ ID NO: | Product, size |
|---|---|---|
| 5' SA0037 SEQ ID NO: 1 | ATGAATACAATCAAAACTACGAAA | Conserved hypothetical protein, 519 bp |
| 3' SA0037 SEQ ID NO: 2 | CTTCTCATCGTCATCTGATTTCAAAATCCATTTTTGA | |
| 5' Lipase SEQ ID NO: 3 | ACTCTA<u>GGTCTCA</u>CTCCCATCTGAAACAATTATGACCAAAT | Lipase, 966 bp |
| 3' Lipase SEQ ID NO: 4 | ATGGTA<u>GGTCTCA</u>TATCATAAAGGATTTAACGGTAATTCATTACT | |
| 5' SA0688 SEQ ID NO: 5 | ATGGTA<u>GGTCTCA</u>CTCCGATAAGTCAAATGGCAAACTAAAAGT | ABC trans. lipoprotein, 860 bp |
| 3' SA0688 SEQ ID NO: 6 | ATGGTA<u>GGTCTCA</u>TATCATTTCATGCTTCCGTGTACAGTT | |
| 5' Glucosaminidase SEQ ID NO: 7 | ATGGTA<u>GGTCTCA</u>CTCCGCTTATACTGTTACTAAACCACAAAC | Glucosaminidase, 1443 bp |
| 3' Glucosaminidase SEQ ID NO: 8 | ATGGTA<u>GGTCTCA</u>TATCATTTATATTGTGGGATGTCGAAGTATT | |
| 5' SA0486 SEQ ID NO: 9 | ACTCTA<u>GGTCTCA</u>CTCCAAAGAAGATTCAAAAGAAGAACAAAT | Hypothetical lipoprotein, 683 bp |
| 3' SA0486 SEQ ID NO: 10 | ATGGTA<u>GGTCTCA</u>TATCAGCTATCTTCATCAGACGGCCCA | |
| 5' SA0119 SEQ ID NO: 11 | CATGCCATGGACACGACTTCAATGAATG | Putative uncharacterized protein, 726 bp |
| 3' SA0119 SEQ ID NO: 12 | AGCTTTGTTTAAACTCAATGATGATGATGATGATGAACTTTTTTGTTACTTTGGTTC | |

BsaI sites are underlined in primers.

The PCR products were cloned into pBAD-Thio/TOPO (SACOL0037 and SACOL0119) or pASK-IBA14 (SACOL0486, SACOL0688, and glucosaminidase), transformed into TOP10 *E. coli*, and sequenced. Details regarding the plasmids are provided in Table 3.

TABLE 3

Plasmids utilized in this study.

| Plasmid | Genotype or Characteristics | Source |
|---|---|---|
| pBAD-Thio/TOPO | 4454 bp pUC ori, Amp$^R$, pBAD promoter, for arabinose-inducible expression of PCR product | Invitrogen Life Technologies |
| pASK-IBA14 | 3001 bp pUC ori, Amp$^R$, tetA promoter, for tetracycline-inducible expression of PCR product | IBA, Gottingen, Germany |

The clones were then expressed using either arabinose induction (SACOL0037 and SACOL0119) or anhydrotetracycline induction (all others). SACOL0037 and SACOL0119 were purified via ProBond cobalt affinity chromatography (Invitrogen, Life technologies, Carlsbad, Calif.), while all other antigens were purified using Strep-Tactin Superflow Columns (IBA, Gottingen, Germany). Purity was confirmed by resolving each protein on 10-20% SDS-PAGE and quantities were determined by BCA (Pierce, Rockford Ill.). Desalting and buffer exchange to phosphate-buffered saline (PBS) was performed for SACOL0486, SACOL0688, and glucosaminidase using 30 kDa molecular weight cut-off (MWCO) Amicon filtration units (Millipore, Billerica, Mass.) per the manufacturer's instructions. Desalting and buffer exchange to PBS was performed for SACOL0119 using 10 kDa MWCO Amicon filtration units (Millipore, Billerica, Mass.). Desalting of SACOL0037 into Nano-pure water was achieved using desalting PD-10 columns (GE Healthcare, Waukesha, Wis.) following the manufacturer's procedure. Subsequently, SACOL0037 was lyophilized using a Virtis freezer dryer (SP Scientific, Warminster, Pa.) and the protein particulate was reconstituted in PBS. Protein quantities were determined by BCA (Pierce, Rockland, Ill.) and confirmed by resolving the proteins on 10-20% SDS-PAGE.

Surgical implantation of pins. Four to eight mice per experimental group (performed in duplicate) were either non-vaccinated with alum adjuvant alone or vaccinated with the quadrivalent biofilm vaccine, the single additional antigen (SA0119), or the combination of all tested antigens (pentavalent vaccine) at 12.5 µg/antigen in alum adjuvant. Vaccines were administered by intraperitoneal (IP) injection Animals were boosted 14 days later with a non-vaccinated treatment of PBS or vaccinated treatment with the above vaccine compositions suspended in straight PBS. 14 days following boost, mice were anesthetized via IP injection of 100 mg/kg ketamine (Ketaset®—Fort Dodge Laboratories, Inc., Fort Dodge, Iowa) and 10 mg/kg xylazine (Rugby Laboratories, Inc., Rockville Center, N.Y.). The left leg of each mouse was cleansed with povidone iodine and rinsed with 70% ethanol before surgical implantation of an sterile 0.25-mm insect pins (Fine Science Tools, Foster City, Calif.) according to the methods previously described (35, 49). Following implantation, 1 µl of the 1×10$^6$ CFU/ml *S. aureus* suspension prepared above was directly inoculated onto the pin implant followed by incision closure. Since 100 CFUs of *S. aureus* are capable of causing chronic infection in this model (data not shown) and in foreign body infections in humans (19), this infectious dose is at least ten times that required to cause infection. All mice did not undergo any additional treatments after surgery until sacrifice. All animal experiments were performed in accordance to protocols reviewed and approved by the Institutional Animal Care and Use Committee (IACUC) at the University of Maryland School of Medicine (Baltimore, Md.).

Bone Cultures. In order to demonstrate animal model efficacy, At 4, 7, 14, 21, 28, and 49 days post-implantation, infected and uninfected mice were euthanized, left tibiae were removed, and all soft tissue was dissected from the bone. Using sterile scissors, tibiae were cut into small pieces and placed in 300 µl of sterile 0.85% saline per 100 µg of bone. Bones were homogenized using a Polytron PT 1200 handheld homogenizer (Kinematica, Bohemia, N.Y.) and serial 10-fold dilutions of bone homogenates were plated on tryptic soy blood agar plates to enumerate viable *S. aureus* per g bone and CHROMagar MRSA plates (CHROMagar, Paris, France) to verify a monomicrobial *S. aureus* infection. In addition, non-vaccinated mice (alum alone) and mice vaccinated with the quadrivalent vaccine, the single additional antigen SA0119, or all antigens combined were euthanized at 21 days post infection and tibial colony-forming units (CFUs) were determined as described above. Dissemination of the *S. aureus* infection was monitored by homogenizing kidneys and plating the homogenates as described above.

PNA-FISH Biofilm Detection on Explanted Pins. In order to demonstrate biofilms on infected pins in the tibia of mice, the pins from infected and uninfected mice were carefully removed from the tibiae to prevent perturbation of biofilm mass at 7 and 21 days post-implantation. Pins were fixed in 2% paraformaldehyde in PBS before PNA-FISH hybridization with a FITC-labeled *S. aureus* probe and a rhodamine-labeled universal eukaryotic cell probe, as per manufacturer's instructions (Advandx, Woburn, Mass.). Each pin was then examined with a Zeiss LSM 510 confocal scanning laser microscope (Carl Zeiss, Thornwood, N.Y.) for both green and red fluorescence using a FITC/Texas Red dual-band filter and a 63× objective.

Statistical Analysis. Mean and SD were calculated and analyzed using Student's t-test with a P value of <0.05 to determine statistical significance. Experiments determining the percentage of mice still infected after vancomycin or PBS treatment were analyzed using Fishers Exact test with a p value of <0.05 for statistical significance.

Results

*S. aureus* implant infection results in chronic infection. Tibiae from mice with pins infected with *S. aureus* and control tibiae with non-infected pins were harvested and processed at 4, 7, 14, 21, 28, and 49 days post-implantation. CFUs were enumerated from homogenized bone to determine the development of chronic infection and bacterial loads in the tibia. Results demonstrate that viable *S. aureus* were cultured from the *S. aureus* infected pin and surrounding bone at all time points tested, as far out as 49 days post-infection (FIG. 1). Bacterial loads initially increased to over 3 logs of the infecting dose to >10$^8$ CFU/tibia but then decreased between 4 and 7 days post-infection. However, at day 7 and beyond, bacterial loads were consistent. Biofilm formation was evident on implanted pins from infected (see FIG. 1B) but not uninfected mice (see FIG. 1C,D) by confocal scanning laser microscopy.

Figure 2:
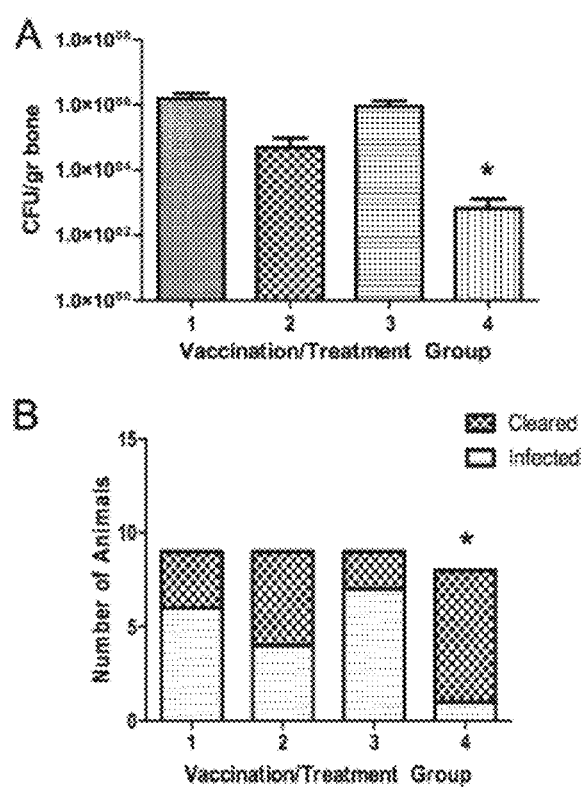
FIG. 2: Vaccination with quadrivalent vaccine and adjunctive vancomycin treatment in a rabbit model of an S. aureus osteomyelitis biofilm infection. (A) Animals vaccinated with PBS only (1), PBS and subsequent treatment with vancomycin (2), the quadrivalent vaccine only (3), or the vaccine plus vancomycin (4). The mean+/−SEM for CFU/grams bone is shown for each group. *=significant difference from group 1, PBS control (P<0.05, Student's t test). (B) Animals in each group that were completely cleared of infection. *=significant difference from group 1, PBS control (P<0.05, Fisher's Exact Test).

Vaccination with biofilm-upregulated antigens coupled with antibiotic therapy promotes clearance of a *S. aureus* osteomyelitis infection. In previous work, Brady et al. identified candidate proteins that were upregulated during the biofilm mode of growth and highly immunogenic in rabbits to formulate a multivalent vaccine against *S. aureus* biofilm-mediated infections (4). In an initial vaccination trial, a quadrivalent vaccine composed of SACOL0486, SACOL0688, SACOL0037, and glucosaminidase (10 µg per recombinant protein) was injected into rabbits at 20 and 10 days prior to challenge using a *S. aureus* tibial osteomyelitis infection. Vaccinated rabbits had a slight reduction in bacterial load at 14 days post-infection compared to control animals, but bacterial clearance was not achieved (data not shown/Brady 2011). While the quadrivalent vaccine targets the *S. aureus* biofilm, its components do not activate an effective humoral response against *S. aureus* planktonic cells and these bacteria persist at day 14 post-infection due to the expression of immunoavoidance factors. Hence, the vaccination strategy was adapted by adding a 10 day vancomycin treatment course starting 14 days post-challenge to eradicate the antibiotic-sensitive, planktonic bacteria dispersed from the biofilm. To evaluate the efficacy of the dual therapy, *S. aureus* enumeration (FIG. 2A) and clearance rates (FIG. 2B) in rabbits of the dual therapy group were compared with those in unvaccinated and untreated, unvaccinated but treated, and vaccinated but untreated groups. Significant reductions in both bacterial counts and infection rate were observed with the dual therapy (column 4), which establishes that targeting the planktonic phenotype of *S. aureus* is critical to eradicate a biofilm-mediated infection. Overall, a 99.9% reduction in the bacterial population was observed in vaccinated animals compared to control animals.

Figure 3:
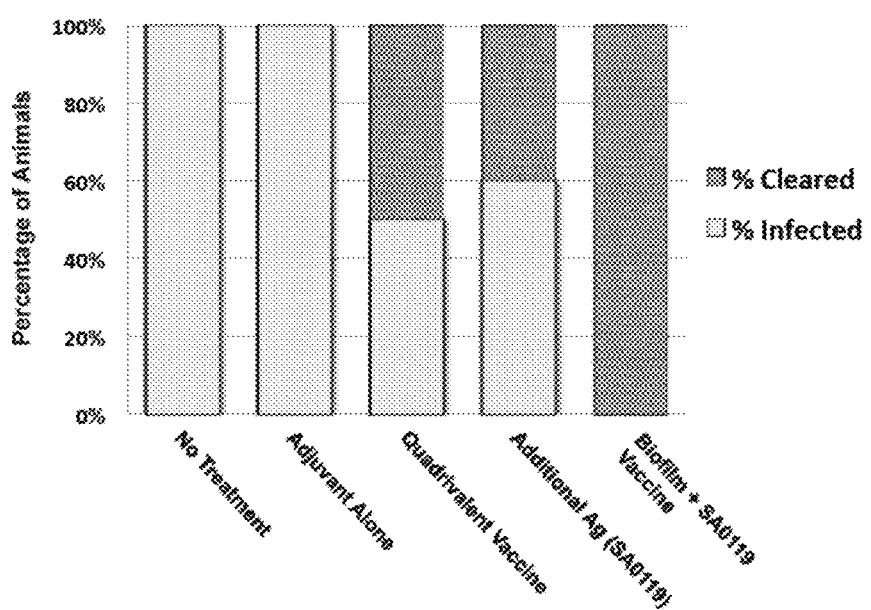
FIG. 3: Vaccination with quadrivalent biofilm vaccine, planktonic vaccine, or pentavalent dual phenotype vaccine in a murine model of a S. aureus implant infection. Control mice received no treatment (column 1) or unvaccinated with Alum alone (column 2). Experimental mice received a biofilm-directed quadrivalent vaccine (column 3), a planktonic-specific monovalent vaccine (SA0119; column 4), or a combination of the antigens in a pentavalent vaccine (column 5).

Vaccination with a pentavalent vaccine composed of biofilm-upregulated and planktonic-specific antigens promotes clearance of a *S. aureus* tibial implant infection. As an extension of the vaccine study in the rabbit tibial osteomyelitis model, we targeted the planktonic phenotype of a *S. aureus* infection with the addition of a planktonic-specific antigen, SACOL0119, to the biofilm-directed quadrivalent vaccine (SACOL0486, SACOL0688, SACOL0037, and glucosaminidase). The efficacy of this pentavalent vaccine against *S. aureus* infection was evaluated using a murine tibial implant model, which is a critical evaluation of the vaccine against another biofilm-mediated infection besides osteomyelitis. The pentavalent vaccine, which was composed of 12.5 µg of each recombinant antigen, was administered at 28 and 14 days prior to *S. aureus* challenge using the tibial implant model. At 21 days post-challenge, CFUs in the tibiae from mice vaccinated with the pentavalent vaccine were enumerated and compared to counts from mice vaccinated with either the quadrivalent vaccine or monovalent SACOL0119 vaccine and unvaccinated mice. Kidney homogenates were also examined for bacterial counts. We did not observed *S. aureus* in the kidneys of any control or experimental animals, which confirms that the infections were localized and did not disseminate from the tibia. In the unvaccinated mice, we observed a 100% infection rate (FIG. 3) and the development of an involucrum around the implant insertion site (data not shown). The quadrivalent vaccine and the SACOL0119 vaccine provided partial protection against *S. aureus* infection with bacterial clearance observed in 50% and 40% of the animals, respectively (FIG. 3). In the quadrivalent and SACOL0119 vaccinated mice, the presence of an involucrum on the tibia corresponded with the presence of *S. aureus* at the implant site. Since vaccination with either the biofilm-upregulated antigens or the planktonic-specific antigen alone provide approximately equivalent protection, we surmised that a combination of the antigens would have a synergistic effect and provide complete clearance of *S. aureus* in the tibial implant model. The addition of this planktonic antigen would substitute for the use an adjunctive antibiotic therapy to eradicate persisting *S. aureus* as previously demonstrated by our lab. Indeed, the pentavalent vaccine provided complete protection against *S. aureus* with 100% clearance in all mice within this vaccine subgroup (FIG. 3). Additionally, tibiae from the pentavalent vaccinated mice resembled uninfected tibiae with no signs of infection. Therefore, the incorporation of the single planktonic antigen to the multivalent biofilm-directed vaccine enhanced the vaccine efficacy from 50% to 100% prevention of a biofilm-mediated, implant infection in C57BL/6J mice. Here, we achieved complete bacterial clearance of *S. aureus*, which is an accomplishment that has never been attained with other vaccine formulations including those that advanced into clinical trials, using a vaccination strategy that targeted both the planktonic and biofilm phenotypes of the pathogen.

REFERENCES

All documents, papers and published materials referenced herein, including books, journal articles, manuals, patent applications, published patent applications and patents, are expressly incorporated herein by reference in their entireties.

1. Arciola, C. R., M. Cervellati, V. Pirini, S. Gamberini, and L. Montanaro. 2001/10. Staphylococci in orthopaedic surgical wounds. New Microbiol. 24:365-369.
2. Arrecubieta, C., I. Matsunaga, T. Asai, Y. Naka, M. C. Deng, and F. D. Lowy. 2008. Vaccination with clumping factor A and fibronectin binding protein A to prevent *Staphylococcus aureus* infection of an aortic patch in mice. J Infect Dis 198:571-5.
3. Assenmacher, M., M. Lohning, A. Scheffold, R. A. Manz, J. Schmitz, and A. Radbruch. 1998. Sequential production of IL-2, IFN-gamma and IL-10 by individual staphylococcal enterotoxin B-activated T helper lymphocytes. Eur J Immunol 28:1534-43.
4. Benton, B. M., J. P. Zhang, S. Bond, C. Pope, T. Christian, L. Lee, K. M. Winterberg, M. B. Schmid, and J. M. Buysse. 2004/12. Large-scale identification of genes required for full virulence of *Staphylococcus aureus*. J. Bacteriol. 186: 8478-8489.
5. Brady, R. A., J. G. Leid, A. K. Camper, J. W. Costerton, and M. E. Shirtliff. 2006. Identification of *Staphylococcus aureus* proteins recognized by the antibody-mediated immune response to a biofilm infection. Infection and Immunity 74:3415-26.
6. Brady, R. A., G. A. O'May, J. G. Leid, M. L. Prior, J. W. Costerton, and M. E. Shirtliff. 2011. Resolution of *Staphylococcus aureus* biofilm infection using vaccination and antibiotic treatment. Infection and Immunity 79:1797-803.
7. Breuer, K., M. Wittmann, K. Kempe, A. Kapp, U. Mai, O. Dittrich-Breiholz, M. Kracht, S. Mrabet-Dahbi, and T. Werfel. 2005. Alpha-toxin is produced by skin colonizing *Staphylococcus aureus* and induces a T helper type 1 response in atopic dermatitis. Clin Exp Allergy 35:1088-95.
8. Brown, E. L., O. Dumitrescu, D. Thomas, C. Badiou, E. M. Koers, P. Choudhury, V. Vazquez, J. Etienne, G. Lina, F. Vandenesch, and M. G. Bowden. 2009. The Panton-Valentine leukocidin vaccine protects mice against lung and skin infections caused by *Staphylococcus aureus* USA300. Clin Microbiol Infect 15:156-64.
9. Bubeck Wardenburg, J., and O. Schneewind. 2008. Vaccine protection against *Staphylococcus aureus* pneumonia. J Exp Med 205:287-94.
10. Capparelli, R., N. Nocerino, C. Medaglia, G. Blaiotta, P. Bonelli, and D. Iannelli. 2011. The *Staphylococcus aureus* peptidoglycan protects mice against the pathogen and eradicates experimentally induced infection. PLoS One 6:e28377.
11. Cerca, N., K. K. Jefferson, T. Maira-Litran, D. B. Pier, C. Kelly-Quintos, D. A. Goldmann, J. Azeredo, and G. B. Pier. 2007. Molecular basis for preferential protective efficacy of antibodies directed to the poorly acetylated form of staphylococcal poly-N-acetyl-beta-(1-6)-glucosamine Infect Immun 75:3406-13.
12. Cocchiaro, J. L., M. I. Gomez, A. Risley, R. Solinga, D. O. Sordelli, and J. C. Lee. 2006. Molecular characterization of the capsule locus from non-typeable *Staphylococcus aureus*. Mol Microbiol 59:948-60.
13. Costerton, J. W., P. S. Stewart, and E. P. Greenberg. 1999/5/21. Bacterial biofilms: a common cause of persistent infections. Science. 284:1318-1322.
14. Dale, S. E., A. Doherty-Kirby, G. Lajoie, and D. E. Heinrichs. 2004. Role of siderophore biosynthesis in virulence of *Staphylococcus aureus*: identification and characterization of genes involved in production of a siderophore. Infect Immun 72:29-37.
15. Dauwalder, O., D. Thomas, T. Ferry, A. L. Debard, C. Badiou, F. Vandenesch, J. Etienne, G. Lina, and G. Monneret. 2006. Comparative inflammatory properties of staphylococcal superantigenic enterotoxins SEA and SEG: implications for septic shock. J Leukoc Biol 80:753-8.
16. Dedent, A., H. K. Kim, D. Missiakas, and O. Schneewind. 2012. Exploring *Staphylococcus aureus* pathways to disease for vaccine development. Semin Immunopathol 34:317-33.
17. Donlan, R. M., and J. W. Costerton. 2002/4. Biofilms: survival mechanisms of clinically relevant microorganisms. Clin. Microbiol. Rev. 15:167-193.
18. Dryla, A., D. Gelbmann, A. von Gabain, and E. Nagy. 2003. Identification of a novel iron regulated staphylococcal surface protein with haptoglobin-haemoglobin binding activity. Mol Microbiol 49:37-53.
19. Elek, S. D. 1956. Experimental staphylococcal infections in the skin of man. Annals of the New York Academy of Sciences 65:85-90.
20. Fattom, A. I., J. Sarwar, A. Ortiz, and R. Naso. 1996. A *Staphylococcus aureus* capsular polysaccharide (CP) vaccine and CP-specific antibodies protect mice against bacterial challenge. Infect Immun 64:1659-65.
21. Fedtke, I., F. Gotz, and A. Peschel. 2004/9. Bacterial evasion of innate host defenses—the *Staphylococcus aureus* lesson. Int. J. Med. Microbiol 294:189-194.
22. Gening, M. L., T. Maira-Litran, A. Kropec, D. Skurnik, M. Grout, Y. E. Tsvetkov, N. E. Nifantiev, and G. B. Pier. 2010. Synthetic {beta}-(1→6)-linked N-acetylated and nonacetylated oligoglucosamines used to produce conjugate vaccines for bacterial pathogens. Infect Immun 78:764-72.
23. Gresham, H. D., J. H. Lowrance, T. E. Caver, B. S. Wilson, A. L. Cheung, and F. P. Lindberg. 2000. Survival of *Staphylococcus aureus* inside neutrophils contributes to infection. J Immunol 164:3713-22.

24. Grundmann, H., M. ires-de-Sousa, J. Boyce, and E. Tiemersma. 2006/9/2. Emergence and resurgence of meticillin-resistant *Staphylococcus aureus* as a public-health threat. Lancet. 368:874-885.
25. Harro, C. D., R. F. Betts, J. S. Hartzel, M. T. Onorato, J. Lipka, S. S. Smugar, and N. A. Kartsonis. 2012. The immunogenicity and safety of different formulations of a novel *Staphylococcus aureus* vaccine (V710): Results of two Phase I studies. Vaccine 30:1729-36.
26. Horan, T. C., D. H. Culver, R. P. Gaynes, W. R. Jarvis, J. R. Edwards, and C. R. Reid. 1993/2. Nosocomial infections in surgical patients in the United States, January 1986-June 1992. National Nosocomial Infections Surveillance (NNIS) System. Infect. Control Hosp. Epidemiol. 14:73-80.
27. Josefsson, E., O. Hartford, L. O'Brien, J. M. Patti, and T. Foster. 2001. Protection against experimental *Staphylococcus aureus* arthritis by vaccination with clumping factor A, a novel virulence determinant. J Infect Dis 184:1572-80.
28. Joyce, J. G., C. Abeygunawardana, Q. Xu, J. C. Cook, R. Hepler, C. T. Przysiecki, K. M. Grimm, K. Roper, C. C. Ip, L. Cope, D. Montgomery, M. Chang, S. Campie, M. Brown, T. B. McNeely, J. Zorman, T. Maira-Litran, G. B. Pier, P. M. Keller, K. U. Jansen, and G. E. Mark. 2003. Isolation, structural characterization, and immunological evaluation of a high-molecular-weight exopolysaccharide from *Staphylococcus aureus*. Carbohydr Res 338:903-22.
29. Kennedy, A. D., J. Bubeck Wardenburg, D. J. Gardner, D. Long, A. R. Whitney, K. R. Braughton, O. Schneewind, and F. R. DeLeo. 2010. Targeting of alpha-hemolysin by active or passive immunization decreases severity of USA300 skin infection in a mouse model. J Infect Dis 202:1050-8.
30. Kim, H. K., A. DeDent, A. G. Cheng, M. McAdow, F. Bagnoli, D. M. Missiakas, and O. Schneewind. 2010. IsdA and IsdB antibodies protect mice against *Staphylococcus aureus* abscess formation and lethal challenge. Vaccine 28:6382-92.
31. Klevens, R. M., M. A. Morrison, J. Nadle, S. Petit, K. Gershman, S. Ray, L. H. Harrison, R. Lynfield, G. Dumyati, J. M. Townes, A. S. Craig, E. R. Zell, G. E. Fosheim, L. K. McDougal, R. B. Carey, and S. K. Fridkin. 2007/10/17. Invasive methicillin-resistant *Staphylococcus aureus* infections in the United States. JAMA. 298:1763-1771.
32. Knobloch, J. K., M. A. Horstkotte, H. Rohde, and D. Mack. 2002. Evaluation of different detection methods of biofilm formation in *Staphylococcus aureus*. Med Microbiol Immunol 191:101-6.
33. Kuklin, N. A., D. J. Clark, S. Secore, J. Cook, L. D. Cope, T. McNeely, L. Noble, M. J. Brown, J. K. Zorman, X. M. Wang, G. Pancari, H. Fan, K. Isett, B. Burgess, J. Bryan, M. Brownlow, H. George, M. Meinz, M. E. Liddell, R. Kelly, L. Schultz, D. Montgomery, J. Onishi, M. Losada, M. Martin, T. Ebert, C. Y. Tan, T. L. Schofield, E. Nagy, A. Meineke, J. G. Joyce, M. B. Kurtz, M. J. Caulfield, K. U. Jansen, W. McClements, and A. S. Anderson. 2006. A novel *Staphylococcus aureus* vaccine: iron surface determinant B induces rapid antibody responses in rhesus macaques and specific increased survival in a murine *S. aureus* sepsis model. Infect Immun 74:2215-23.
34. Leid, J. G., M. E. Shirtliff, J. W. Costerton, and A. P. Stoodley. 2002. Human leukocytes adhere to, penetrate, and respond to *Staphylococcus aureus* bilfilms. Infection and Immunity 70:6339-45.
35. Li, D., K. Gromov, K. Soballe, J. E. Puzas, R. J. O'Keefe, H. Awad, H. Drissi, and E. M. Schwarz. 2008/1. Quantitative mouse model of implant-associated osteomyelitis and the kinetics of microbial growth, osteolysis, and humoral immunity. J Orthop. Res. 26:96-105.
36. Lindsay, J. A., and M. T. Holden. 2004/8. *Staphylococcus aureus*: superbug, super genome? Trends Microbiol 12:378-385.
37. Mader, J. T., and M. E. Shirtliff. 1999. The rabbit model of bacterial osteomyelitis of the tibia. Academic Press Ltd., London, England.
38. Maira-Litran, T., A. Kropec, D. A. Goldmann, and G. B. Pier. 2005. Comparative opsonic and protective activities of *Staphylococcus aureus* conjugate vaccines containing native or deacetylated Staphylococcal Poly-N-acetyl-beta-(1-6)-glucosamine. Infect Immun 73:6752-62.
39. McCarthy, A. J., and J. A. Lindsay. 2010. Genetic variation in *Staphylococcus aureus* surface and immune evasion genes is lineage associated: implications for vaccine design and host-pathogen interactions. BMC Microbiol 10:173.
40. McKenney, D., J. Hubner, E. Muller, Y. Wang, D. A. Goldmann, and G. B. Pier. 1998. The ica locus of *Staphylococcus epidermidis* encodes production of the capsular polysaccharide/adhesin. Infect Immun 66:4711-20.
41. McKenney, D., K. L. Pouliot, Y. Wang, V. Murthy, M. Ulrich, G. Doring, J. C. Lee, D. A. Goldmann, and G. B. Pier. 1999. Broadly protective vaccine for *Staphylococcus aureus* based on an in vivo-expressed antigen. Science 284:1523-7.
42. Megyeri, K., Y. Mandi, M. Degre, and I. Rosztoczy. 2002. Induction of cytokine production by different Staphylococcal strains. Cytokine 19:206-12.
43. Modun, B., R. W. Evans, C. L. Joannou, and P. Williams. 1998. Receptor-mediated recognition and uptake of iron from human transferrin by *Staphylococcus aureus* and *Staphylococcus epidermidis*. Infect Immun 66:3591-6.
44. Ni Eidhin, D., S. Perkins, P. Francois, P. Vaudaux, M. Hook, and T. J. Foster. 1998. Clumping factor B (ClfB), a new surface-located fibrinogen-binding adhesin of *Staphylococcus aureus*. Mol Microbiol 30:245-57.
45. Nippe, N., G. Varga, D. Holzinger, B. Loffler, E. Medina, K. Becker, J. Roth, J. M. Ehrchen, and C. Sunderkotter. 2011. Subcutaneous infection with *S. aureus* in mice reveals association of resistance with influx of neutrophils and Th2 response. J Invest Dermatol 131:125-32.
46. Nishimura, S., T. Tsurumoto, A. Yonekura, K. Adachi, and H. Shindo. 2006. Antimicrobial susceptibility of *Staphylococcus aureus* and *Staphylococcus epidermidis* biofilms isolated from infected total hip arthroplasty cases. J Orthop Sci 11:46-50.
47. Peters, B. M., M. A. Jabra-Rizk, M. A. Scheper, J. G. Leid, J. W. Costerton, and M. E. Shirtliff. Microbial interactions and differential protein expression in *Staphylococcus aureus-Candida albicans* dual-species biofilms. FEMS Immunol Med Microbiol 59:493-503.
48. Pohlmann-Dietze, P., M. Ulrich, K. B. Kiser, G. Doring, J. C. Lee, J. M. Fournier, K. Botzenhart, and C. Wolz. 2000. Adherence of *Staphylococcus aureus* to endothelial cells: influence of capsular polysaccharide, global regulator agr, and bacterial growth phase. Infect Immun 68:4865-71.
49. Prabhakara, R., J. M. Harro, J. G. Leid, M. Harris, and M. E. Shirtliff. 2011. Murine immune response to a chronic *Staphylococcus aureus* biofilm infection. Infection and Immunity 79:1789-96.
50. Prabhakara, R., J. M. Harro, J. G. Leid, A. D. Keegan, M. L. Prior, and M. E. Shirtliff. 2011. Suppression of the Inflammatory Immune Response Prevents the Development of Chronic Biofilm Infection Due to Methicillin-Resistant *Staphylococcus aureus*. Infection and Immunity 79:5010-8.
51. Raad, I. I., R. Darouiche, R. Hachem, M. Sacilowski, and G. P. Bodey. 1995. Antibiotics and prevention of microbial colonization of catheters. Antimicrobial Agents and Chemotherapy 39:2397-400.
52. Raedler, M. D., S. Heyne, E. Wagner, S. K. Shalkowski, S. Secore, A. S. Anderson, J. Cook, L. Cope, T. McNeely, M. Retzlaff, J. Shanter, L. J. Rubinstein, T. Green, N. Kartsonis, and M. T. Esser. 2009. Serologic assay to quantify human immunoglobulin G antibodies to the *Staphylococcus aureus* iron surface determinant B antigen. Clin Vaccine Immunol 16:739-48.
53. Rohde, H., J. K. Knobloch, M. A. Horstkotte, and D. Mack. 2001. Correlation of *Staphylococcus aureus* icaADBC genotype and biofilm expression phenotype. J Clin Microbiol 39:4595-6.
54. Sanderson, P. J. 1991. Infection in orthopaedic implants. Journal of Hospital Infection 18 Suppl A:367-75.
55. Saravia-Otten, P., H. P. Muller, and S. Arvidson. 1997. Transcription of *Staphylococcus aureus* fibronectin binding protein genes is negatively regulated by agr and an agr-independent mechanism. J Bacteriol 179:5259-63.
56. Schaffer, A. C., and J. C. Lee. 2008. Vaccination and passive immunisation against *Staphylococcus aureus*. Int J Antimicrob Agents 32 Suppl 1:S71-8.
57. Schaffer, A. C., R. M. Solinga, J. Cocchiaro, M. Portoles, K. B. Kiser, A. Risley, S. M. Randall, V. Valtulina, P. Speziale, E. Walsh, T. Foster, and J. C. Lee. 2006. Immunization with *Staphylococcus aureus* clumping factor B, a major determinant in nasal carriage, reduces nasal colonization in a murine model. Infect Immun 74:2145-53.
58. Sebulsky, M. T., D. Hohnstein, M. D. Hunter, and D. E. Heinrichs. 2000. Identification and characterization of a membrane permease involved in iron-hydroxamate transport in *Staphylococcus aureus*. J Bacteriol 182:4394-400.
59. Shinefield, H., S. Black, A. Fattom, G. Horwith, S. Rasgon, J. Ordonez, H. Yeoh, D. Law, J. B. Robbins, R. Schneerson, L. Muenz, S. Fuller, J. Johnson, B. Fireman, H. Alcorn, and R. Naso. 2002. Use of a *Staphylococcus aureus* conjugate vaccine in patients receiving hemodialysis. N Engl J Med 346:491-6.
60. Shirtliff, M. E., J. H. Calhoun, and J. T. Mader. 2002. Gatifloxacin efficacy in treatment of experimental methicillin-sensitive *Staphylococcus aureus*-induced osteomyelitis in rabbits. Antimicrob Agents Chemother 46:231-3.
61. Stranger-Jones, Y. K., T. Bae, and O. Schneewind. 2006. Vaccine assembly from surface proteins of *Staphylococcus aureus*. Proc Natl Acad Sci USA 103:16942-7.
62. Torres, V. J., G. Pishchany, M. Humayun, O. Schneewind, and E. P. Skaar. 2006. *Staphylococcus aureus* IsdB is a hemoglobin receptor required for heme iron utilization. J Bacteriol 188:8421-9.
63. von Kockritz-Blickwede, M., M. Rohde, S. Oehmcke, L. S. Miller, A. L. Cheung, H. Herwald, S. Foster, and E. Medina. 2008 Immunological mechanisms underlying the genetic predisposition to severe *Staphylococcus aureus* infection in the mouse model. Am J Pathol 173:1657-68.
64. Wang, R., K. R. Braughton, D. Kretschmer, T. H. Bach, S. Y. Queck, M. Li, A. D. Kennedy, D. W. Dorward, S. J. Klebanoff, A. Peschel, F. R. DeLeo, and M. Otto. 2007/12. Identification of novel cytolytic peptides as key virulence determinants for community-associated MRSA. Nat. Med. 13:1510-1514.
65. Zhou, H., Z. Y. Xiong, H. P. Li, Y. L. Zheng, and Y. Q. Jiang. 2006. An immunogenicity study of a newly fusion protein Cna-FnBP vaccinated against *Staphylococcus aureus* infections in a mice model. Vaccine 24:4830-7.
66. Sauer, K., A. K. Camper, G. D. Ehrlich, J. W. Costerton, and D. G. Davies. 2002. *Pseudomonas aeruginosa* Displays Multiple Phenotypes during Development as a Biofilm. J. Bacteriol. 184:1140-1154.

What is claimed is:

1. An immunogenic composition comprising:
   (a) five purified *Staphylococcus aureus* polypeptides, or portions thereof, or variants thereof, or combinations thereof, wherein the *S. aureus* polypeptides are (i) biofilm-specific *S. aureus* polypeptide SA0037 set forth in SEQ ID NO: 13, (ii) planktonic-specific *S. aureus* polypeptide SA0119 set forth in SEQ ID NO: 14, (iii) biofilm-specific *S. aureus* polypeptide SA0486 set forth in SEQ ID NO: 15, (iv) biofilm-specific *S. aureus* polypeptide SA0688 set forth in SEQ ID NO:16, and (v) biofilm-specific *S. aureus* glucosaminidase set forth in SEQ ID NO: 17, wherein each of the portions is at least 95% of the size of the corresponding full-length polypeptide, and wherein each of the variants has at least 95% sequence identity with the corresponding full-length polypeptide,
   (b) a pharmaceutically acceptable carrier or diluent and
   (c) an immunostimulatory amount of an adjuvant.

2. The composition of claim 1, wherein the five purified *S. aureus* polypeptides are full-length *S. aureus* polypeptides.

3. A formulation comprising an immunologically effective amount of a vaccine comprising:
   (a) five purified *Staphylococcus aureus* polypeptides, wherein the *S. aureus* polypeptides are (i) biofilm-specific *S. aureus* polypeptide SA0037 set forth in SEQ ID NO: 13, (ii) planktonic-specific *S. aureus* polypeptide SA0119 set forth in SEQ ID NO: 14, (iii) biofilm-specific *S. aureus* polypeptide SA0486 set forth in SEQ ID NO: 15, (iv) biofilm-specific *S. aureus* polypeptide SA0688 set forth in SEQ ID NO:16, and (v) biofilm-specific *S. aureus* glucosaminidase set forth in SEQ ID NO: 17,
   (b) a pharmaceutically acceptable carrier or diluent and
   (c) an immunostimulatory amount of an adjuvant.

4. A formulation comprising an immunologically effective amount of a vaccine consisting of:
   (a) five purified *Staphylococcus aureus* polypeptides, wherein the *S. aureus* polypeptides are (i) biofilm-specific *S. aureus* polypeptide SA0037 set forth in SEQ ID NO: 13, (ii) planktonic-specific *S. aureus* polypeptide SA0119 set forth in SEQ ID NO: 14, (iii) biofilm-specific *S. aureus* polypeptide SA0486 set forth in SEQ ID NO: 15, (iv) biofilm-specific *S. aureus* polypeptide SA0688 set forth in SEQ ID NO:16, and (v) biofilm-specific *S. aureus* glucosaminidase set forth in SEQ ID NO: 17,
   (b) a pharmaceutically acceptable carrier or diluent and
   (c) an immunostimulatory amount of an adjuvant.

5. A method of generating an immune response against *S. aureus* in a subject comprising administering to the subject an immunologically effective amount of the formulation of claim 3.

6. A method of generating an immune response against *S. aureus* in a subject comprising administering to the subject an immunologically effective amount of the formulation of claim 4.

7. A formulation comprising an immunologically effective amount of a pentavalent vaccine consisting of:
   (a) five purified *Staphylococcus aureus* polypeptides, wherein the *S. aureus* polypeptides are (i) biofilm-specific *S. aureus* polypeptide SA0037 set forth in SEQ ID NO: 13, (ii) planktonic-specific *S. aureus* polypeptide SA0119 set forth in SEQ ID NO: 14, (iii) biofilm-specific *S. aureus* polypeptide SA0486 set forth in SEQ ID NO: 15, (iv) biofilm-specific *S. aureus* polypeptide SA0688 set forth in SEQ ID NO:16, and (v) biofilm-specific *S. aureus* glucosaminidase set forth in SEQ ID NO: 17, and
   (b) a pharmaceutically acceptable carrier or diluent, wherein the vaccine elicits complete protection against a biofilm-associated *S. aureus* implant infection in a mammal with 100% clearance of the infecting *S. aureus*.

8. A method of eliciting a protective immune response against a biofilm-associated *S. aureus* implant infection in a mammal comprising administering to the mammal an immunologically effective amount of the formulation of claim 7.

* * * * *

SEQUENCE LISTING

```
<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: 5' SA0037 PCR primer

<400> SEQUENCE: 1
atgaatacaa tcaaaactac gaaa                                              24

<210> SEQ ID NO 2
<211> LENGTH: 37
<212> TYPE: DNA
<213> ORGANISM: Artificial Sequence
<220> FEATURE:
<223> OTHER INFORMATION: 3' SA0037 PCR primer

<400> SEQUENCE: 2
cttctcatcg tcatctgatt tcaaaatcca tttttga                                37

<210> SEQ ID NO 3
<211> LENGTH: 43
<212> TYPE: DNA
<213> ORGANISM: Artificial Sequence
```

```
<220> FEATURE:
<223> OTHER INFORMATION: 5' Lipase PCR primer

<400> SEQUENCE: 3
actctaggtc tcactcccat ctgaaacaac attatgacca aat                   43

<210> SEQ ID NO 4
<211> LENGTH: 45
<212> TYPE: DNA
<213> ORGANISM: Artificial Sequence
<220> FEATURE:
<223> OTHER INFORMATION: 3' Lipase PCR primer

<400> SEQUENCE: 4
atggtaggtc tcatatcata aaggatttaa cggtaattca ttact                 45

<210> SEQ ID NO 5
<211> LENGTH: 43
<212> TYPE: DNA
<213> ORGANISM: Artificial Sequence
<220> FEATURE:
<223> OTHER INFORMATION: 5' SA0688 PCR primer

<400> SEQUENCE: 5
atggtaggtc tcactccgat aagtcaaatg gcaaactaaa agt                   43

<210> SEQ ID NO 6
<211> LENGTH: 40
<212> TYPE: DNA
<213> ORGANISM: Artificial Sequence
<220> FEATURE:
<223> OTHER INFORMATION: 3' SA0688 PCR primer

<400> SEQUENCE: 6
atggtaggtc tcatatcatt tcatgcttcc gtgtacagtt                       40

<210> SEQ ID NO 7
<211> LENGTH: 43
<212> TYPE: DNA
<213> ORGANISM: Artificial Sequence
<220> FEATURE:
<223> OTHER INFORMATION: 5' Glucosaminidase PCR primer

<400> SEQUENCE: 7
atggtaggtc tcactccgct tatactgtta ctaaaccaca aac                   43

<210> SEQ ID NO 8
<211> LENGTH: 44
<212> TYPE: DNA
<213> ORGANISM: Artificial Sequence
<220> FEATURE:
<223> OTHER INFORMATION: 3' Glucosaminidase PCR primer

<400> SEQUENCE: 8
atggtaggtc tcatatcatt tatattgtgg gatgtcgaag tatt                  44

<210> SEQ ID NO 9
<211> LENGTH: 43
<212> TYPE: DNA
<213> ORGANISM: Artificial Sequence
<220> FEATURE:
<223> OTHER INFORMATION: 5' SA0486 PCR primer

<400> SEQUENCE: 9
actctaggtc tcactccaaa gaagattcaa aagaagaaca aat                   43
```

<210> SEQ ID NO 10
<211> LENGTH: 40
<212> TYPE: DNA
<213> ORGANISM: Artificial Sequence
<220> FEATURE:
<223> OTHER INFORMATION: 3' SA0486 PCR primer

<400> SEQUENCE: 10
atggtaggtc tcatatcagc tatcttcatc agacggccca                          40

<210> SEQ ID NO 11
<211> LENGTH: 28
<212> TYPE: DNA
<213> ORGANISM: Artificial Sequence
<220> FEATURE:
<223> OTHER INFORMATION: 5' SA0119 PCR primer

<400> SEQUENCE: 11
catgccatgg acacgacttc aatgaatg                                       28

<210> SEQ ID NO 12
<211> LENGTH: 57
<212> TYPE: DNA
<213> ORGANISM: Artificial Sequence
<220> FEATURE:
<223> OTHER INFORMATION: 3' SA0119 PCR primer

<400> SEQUENCE: 12
agctttgttt aaactcaatg atgatgatga tgatgaactt ttttgttact ttggttc       57

<210> SEQ ID NO 13
<211> LENGTH: 168
<212> TYPE: PRT
<213> ORGANISM: Staphylococcus aureus

<400> SEQUENCE: 13

Met Asn Thr Ile Lys Asn Thr Ile Tyr Thr Glu Ala Ile Phe Ser Lys
1               5                   10                  15

Asp Glu Lys His Arg Tyr Leu Leu Lys Lys Thr Trp Asp Glu Lys Lys
            20                  25                  30

Pro Ala Cys Thr Val Ile Thr Met Tyr Pro His Leu Asp Gly Val Leu
        35                  40                  45

Ser Leu Asp Leu Thr Thr Val Leu Ile Leu Asn Gln Leu Ala Asn Ser
    50                  55                  60

Glu Arg Tyr Gly Ala Val Tyr Leu Val Asn Leu Phe Ser Asn Ile Lys
65                  70                  75                  80

Thr Pro Glu Asn Leu Lys His Ile Lys Glu Pro Tyr Asp Lys His Thr
                85                  90                  95

Asp Ile His Leu Met Lys Ala Ile Ser Glu Ser Asp Thr Val Ile Leu
            100                 105                 110

Ala Tyr Gly Ala Tyr Ala Lys Arg Pro Val Val Glu Arg Val Glu
        115                 120                 125

Gln Val Met Glu Met Leu Lys Pro His Lys Lys Val Lys Lys Leu
    130                 135                 140

Ile Asn Pro Ala Thr Asn Glu Ile Met His Pro Leu Asn Pro Lys Ala
145                 150                 155                 160

Arg Gln Lys Trp Thr Leu Lys Ala
                165

<210> SEQ ID NO 14

```
<211> LENGTH: 241
<212> TYPE: PRT
<213> ORGANISM: Staphylococcus aureus

<400> SEQUENCE: 14

Met Lys Lys Leu Ala Thr Val Gly Ser Leu Ile Val Thr Ser Thr Leu
1               5                   10                  15

Val Phe Ser Ser Met Pro Phe Gln Asn Ala His Ala Asp Thr Thr Ser
                20                  25                  30

Met Asn Val Pro Asn Lys Gln Ser Gln Asn Val Gln His Arg Pro
        35                  40                  45

Tyr Gly Gly Val Val Pro Gln Gly Met Thr Gln Ala Gln Tyr Thr Glu
    50                  55                  60

Leu Glu Lys Thr Leu Pro Gln Leu Ser Ala Gly Ser Asn Met Gln Asp
65                  70                  75                  80

Tyr Asn Met Lys Leu Tyr Asp Ala Thr Gln Asn Ile Ala Asp Lys Tyr
                85                  90                  95

Asn Val Ile Ile Thr Thr Asn Val Gly Val Phe Lys Pro His Ala Val
            100                 105                 110

Arg Asp Met Asn Gly His Ala Leu Pro Leu Thr Lys Asp Gly Asn Phe
        115                 120                 125

Tyr Gln Thr Asn Val Asp Ala Asn Gly Val Asn His Gly Gly Ser Glu
    130                 135                 140

Met Val Gln Asn Lys Thr Gly His Met Ser Gln Gln Asp His Met Asn
145                 150                 155                 160

Gln Asn Thr His Met Asn Gln Gln Pro Gln Ile Gln Gln Gly His Met
                165                 170                 175

Gln Ser Ser Asn His Gln Met Met Ser Pro Lys Ala Asn Met His Ser
            180                 185                 190

Ser Asn His Gln Met Asn Gln Ser Asn Lys Lys Val Leu Pro Ala Ala
        195                 200                 205

Gly Glu Ser Met Thr Ser Ser Ile Leu Thr Ala Ser Ile Ala Ala Leu
    210                 215                 220

Leu Leu Val Ser Gly Leu Phe Leu Ala Phe Arg Arg Arg Ser Thr Asn
225                 230                 235                 240

Lys

<210> SEQ ID NO 15
<211> LENGTH: 270
<212> TYPE: PRT
<213> ORGANISM: Staphylococcus aureus

<400> SEQUENCE: 15

Met Lys Tyr Lys Thr Glu Arg Arg Glu Met Met Gly Asn Ile Lys Ser
1               5                   10                  15

Phe Ala Leu Tyr Ile Ser Ile Leu Leu Leu Ile Val Val Val Ala Gly
                20                  25                  30

Cys Gly Lys Ser Asp Lys Thr Lys Glu Asp Ser Lys Glu Glu Gln Ile
            35                  40                  45

Lys Lys Ser Phe Ala Lys Thr Leu Asp Met Tyr Pro Ile Lys Asn Leu
        50                  55                  60

Glu Asp Leu Tyr Asp Lys Glu Gly Tyr Arg Asp Gly Glu Phe Lys Lys
65                  70                  75                  80

Gly Asp Lys Gly Thr Trp Thr Leu Leu Thr Ser Phe Lys Ser Asn
                85                  90                  95
```

```
Lys Pro Asp Glu Ile Asp Asp Glu Gly Met Val Leu Tyr Leu Asn Arg
                100                 105                 110

Asn Thr Lys Lys Ala Thr Gly Tyr Tyr Phe Val Asn Lys Ile Tyr Asp
            115                 120                 125

Asp Ile Ser Lys Asn Gln Asn Glu Lys Lys Tyr Arg Val Glu Leu Lys
        130                 135                 140

Asn Asn Lys Ile Val Leu Leu Asp Asn Val Glu Asp Lys Leu Lys
145                 150                 155                 160

Gln Lys Ile Glu Asn Phe Lys Phe Phe Ser Gln Tyr Ala Asp Phe Lys
                165                 170                 175

Asp Leu Lys Asn Tyr Gln Asp Gly Ser Ile Thr Thr Asn Glu Asn Ile
            180                 185                 190

Pro Ser Tyr Glu Ala Glu Tyr Lys Leu Asn Asn Ser Asp Glu Asn Val
        195                 200                 205

Lys Lys Leu Arg Asp Ile Tyr Pro Ile Thr Thr Lys Lys Ala Pro Ile
            210                 215                 220

Leu Lys Leu His Ile Asp Gly Asp Ile Lys Gly Ser Val Gly Tyr
225                 230                 235                 240

Lys Lys Ile Glu Tyr Lys Phe Ser Lys Val Lys Asp Gln Glu Thr Thr
                245                 250                 255

Leu Arg Asp Tyr Leu Asn Phe Gly Pro Ser Asp Glu Asp Ser
            260                 265                 270

<210> SEQ ID NO 16
<211> LENGTH: 309
<212> TYPE: PRT
<213> ORGANISM: Staphylococcus aureus

<400> SEQUENCE: 16

Met Lys Lys Leu Val Pro Leu Leu Leu Ala Leu Leu Leu Leu Val Ala
1               5                   10                  15

Ala Cys Gly Thr Gly Gly Lys Gln Ser Ser Asp Lys Ser Asn Gly Lys
                20                  25                  30

Leu Lys Val Val Thr Thr Asn Ser Ile Leu Tyr Asp Met Ala Lys Asn
            35                  40                  45

Val Gly Gly Asp Asn Val Asp Ile His Ser Ile Val Pro Val Gly Gln
        50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
                100                 105                 110

Lys Lys Val Ile Ala Val Ser Lys Asp Val Lys Pro Ile Tyr Leu Asn
            115                 120                 125

Gly Glu Glu Gly Asn Lys Asp Lys Gln Asp Pro His Ala Trp Leu Ser
        130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205
```

```
Phe Lys Tyr Phe Ser Lys Gln Tyr Gly Ile Thr Pro Gly Tyr Ile Trp
        210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Glu Thr Val
290                 295                 300

His Gly Ser Met Lys
305

<210> SEQ ID NO 17
<211> LENGTH: 1257
<212> TYPE: PRT
<213> ORGANISM: Staphylococcus aureus

<400> SEQUENCE: 17

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
    50                  55                  60

Asn Ile Ser Gly Thr Gln Val Tyr Gln Asp Pro Ala Ile Val Gln Pro
65                  70                  75                  80

Lys Ala Ala Asn Lys Thr Gly Asn Ala Gln Val Asn Gln Lys Val Asp
                85                  90                  95

Thr Thr Gln Val Asn Gly Asp Thr Arg Ala Thr Gln Ser Thr Thr Ser
            100                 105                 110

Asn Asn Ala Lys Pro Val Thr Lys Ser Thr Asn Thr Thr Ala Pro Lys
        115                 120                 125

Thr Asn Asn Asn Val Thr Ser Ala Gly Tyr Ser Leu Val Asp Asp Glu
    130                 135                 140

Asp Asp Asn Ser Glu Asn Gln Ile Asn Pro Glu Leu Ile Lys Ser Ala
145                 150                 155                 160

Ala Lys Pro Ala Ala Leu Glu Thr Gln Tyr Lys Ala Ala Pro Lys
                165                 170                 175

Ala Thr Pro Val Ala Pro Lys Ala Lys Thr Glu Ala Thr Pro Lys Val
            180                 185                 190

Thr Thr Phe Ser Ala Ser Ala Gln Pro Arg Ser Ala Ala Ala Pro
        195                 200                 205

Lys Thr Ser Leu Pro Lys Tyr Lys Pro Gln Val Asn Ser Ser Ile Asn
    210                 215                 220

Asp Tyr Ile Arg Lys Asn Leu Lys Ala Pro Lys Ile Glu Glu Asp
225                 230                 235                 240

Tyr Thr Ser Tyr Phe Pro Lys Tyr Ala Tyr Arg Asn Gly Val Gly Arg
                245                 250                 255

Pro Glu Gly Ile Val Val His Asp Thr Ala Asn Asp Arg Ser Thr Ile
```

-continued

```
              260                 265                 270
Asn Gly Glu Ile Ser Tyr Met Lys Asn Asn Tyr Gln Asn Ala Phe Val
            275                 280                 285
His Ala Phe Val Asp Gly Asp Arg Ile Ile Glu Thr Ala Pro Thr Asp
            290                 295                 300
Tyr Leu Ser Trp Gly Val Gly Ala Val Gly Asn Pro Arg Phe Ile Asn
305                 310                 315                 320
Val Glu Ile Val His Thr His Asp Tyr Ala Ser Phe Ala Arg Ser Met
                325                 330                 335
Asn Asn Tyr Ala Asp Tyr Ala Ala Thr Gln Leu Gln Tyr Tyr Gly Leu
            340                 345                 350
Lys Pro Asp Ser Ala Glu Tyr Asp Gly Asn Gly Thr Val Trp Thr His
            355                 360                 365
Tyr Ala Val Ser Lys Tyr Leu Gly Gly Thr Asp His Ala Asp Pro His
            370                 375                 380
Gly Tyr Leu Arg Ser His Asn Tyr Ser Tyr Asp Gln Leu Tyr Asp Leu
385                 390                 395                 400
Ile Asn Glu Lys Tyr Leu Ile Lys Met Gly Lys Val Ala Pro Trp Gly
                405                 410                 415
Thr Gln Ser Thr Thr Pro Thr Thr Pro Ser Lys Pro Ser Thr Pro
            420                 425                 430
Ser Lys Pro Ser Thr Pro Ser Thr Gly Lys Leu Thr Val Ala Ala Asn
            435                 440                 445
Asn Gly Val Ala Gln Ile Lys Pro Thr Asn Ser Gly Leu Tyr Thr Thr
            450                 455                 460
Val Tyr Asp Lys Thr Gly Lys Ala Thr Asn Glu Val Gln Lys Thr Phe
465                 470                 475                 480
Ala Val Ser Lys Thr Ala Thr Leu Gly Asn Gln Lys Phe Tyr Leu Val
                485                 490                 495
Gln Asp Tyr Asn Ser Gly Asn Lys Phe Gly Trp Val Lys Glu Gly Asp
            500                 505                 510
Val Val Tyr Asn Thr Ala Lys Ser Pro Val Asn Val Asn Gln Ser Tyr
            515                 520                 525
Ser Ile Lys Pro Gly Thr Lys Leu Tyr Thr Val Pro Trp Gly Thr Ser
            530                 535                 540
Lys Gln Val Ala Gly Ser Val Ser Gly Ser Gly Asn Gln Thr Phe Lys
545                 550                 555                 560
Ala Ser Lys Gln Gln Ile Asp Lys Ser Ile Tyr Leu Tyr Gly Ser
                565                 570                 575
Val Asn Gly Lys Ser Gly Trp Val Ser Lys Ala Tyr Leu Val Asp Thr
            580                 585                 590
Ala Lys Pro Thr Pro Thr Pro Thr Pro Lys Pro Ser Thr Pro Thr Thr
            595                 600                 605
Asn Asn Lys Leu Thr Val Ser Ser Leu Asn Gly Val Ala Gln Ile Asn
            610                 615                 620
Ala Lys Asn Asn Gly Leu Phe Thr Thr Val Tyr Asp Lys Thr Gly Lys
625                 630                 635                 640
Pro Thr Lys Glu Val Gln Lys Thr Phe Ala Val Thr Lys Glu Ala Ser
                645                 650                 655
Leu Gly Gly Asn Lys Phe Tyr Leu Val Lys Asp Tyr Asn Ser Pro Thr
            660                 665                 670
Leu Ile Gly Trp Val Lys Gln Gly Asp Val Ile Tyr Asn Asn Ala Lys
            675                 680                 685
```

-continued

Ser Pro Val Asn Val Met Gln Thr Tyr Thr Val Lys Pro Gly Thr Lys
690                 695                 700

Leu Tyr Ser Val Pro Trp Gly Thr Lys Gln Glu Ala Gly Ala Val
705                 710                 715                 720

Ser Gly Thr Gly Asn Gln Thr Phe Lys Ala Thr Lys Gln Gln Ile
            725                 730                 735

Asp Lys Ser Ile Tyr Leu Tyr Gly Thr Val Asn Gly Lys Ser Gly Trp
            740                 745                 750

Ile Ser Lys Ala Tyr Leu Ala Val Pro Ala Ala Pro Lys Lys Ala Val
            755                 760                 765

Ala Gln Pro Lys Thr Ala Val Lys Ala Tyr Ala Val Thr Lys Pro Gln
770                 775                 780

Thr Thr Gln Thr Val Ser Lys Ile Ala Gln Val Lys Pro Asn Asn Thr
785                 790                 795                 800

Gly Ile Arg Ala Ser Val Tyr Glu Lys Thr Ala Lys Asn Gly Ala Lys
            805                 810                 815

Tyr Ala Asp Arg Thr Phe Tyr Val Thr Lys Glu Arg Ala His Gly Asn
            820                 825                 830

Glu Thr Tyr Val Leu Leu Asn Asn Thr Ser His Asn Ile Pro Leu Gly
            835                 840                 845

Trp Phe Asn Val Lys Asp Leu Asn Val Gln Asn Leu Gly Lys Glu Val
850                 855                 860

Lys Thr Thr Gln Lys Tyr Thr Val Asn Arg Ser Asn Gly Leu Ser
865                 870                 875                 880

Met Val Pro Trp Gly Thr Lys Asn Gln Val Ile Leu Thr Gly Asn Asn
                885                 890                 895

Ile Ala Gln Gly Thr Phe Asn Ala Thr Lys Gln Val Ser Val Gly Lys
            900                 905                 910

Asp Val Tyr Leu Tyr Gly Thr Ile Asn Asn Arg Thr Gly Trp Val Asn
            915                 920                 925

Ser Lys Asp Leu Thr Ala Pro Thr Ala Val Lys Pro Thr Thr Ser Ala
930                 935                 940

Ala Lys Asp Tyr Asn Tyr Thr Tyr Val Ile Lys Asn Gly Asn Gly Tyr
945                 950                 955                 960

Tyr Tyr Val Thr Pro Asn Ser Asp Thr Ala Lys Tyr Ser Leu Lys Ala
            965                 970                 975

Phe Asn Glu Gln Pro Phe Ala Val Val Lys Glu Gln Val Ile Asn Gly
            980                 985                 990

Gln Thr Trp Tyr Tyr Gly Lys Leu Ser Asn Gly Lys Leu Ala Trp Ile
            995                 1000                1005

Lys Ser Thr Asp Leu Ala Lys Glu Leu Ile Lys Tyr Asn Gln Ile
    1010                1015                1020

Gly Met Thr Leu Asn Gln Val Ala Gln Ile Gln Ala Gly Leu Gln
    1025                1030                1035

Tyr Lys Pro Gln Val Gln Arg Val Pro Gly Lys Trp Thr Asp Ala
    1040                1045                1050

Asn Phe Asn Asp Val Lys His Ala Met Asp Thr Lys Arg Leu Ala
    1055                1060                1065

Gln Asp Pro Ala Leu Lys Tyr Gln Phe Leu Arg Leu Asp Gln Pro
    1070                1075                1080

Gln Asn Ile Ser Ile Asp Lys Ile Asn Gln Phe Leu Lys Gly Lys
    1085                1090                1095

-continued

Gly Val Leu Glu Asn Gln Gly Ala Ala Phe Asn Lys Ala Ala Gln
1100                1105                 1110

Met Tyr Gly Ile Asn Glu Val Tyr Leu Ile Ser His Ala Leu Leu
1115                1120                 1125

Glu Thr Gly Asn Gly Thr Ser Gln Leu Ala Lys Gly Ala Asp Val
1130                1135                 1140

Val Asn Asn Lys Val Val Thr Asn Ser Asn Thr Lys Tyr His Asn
1145                1150                 1155

Val Phe Gly Ile Ala Ala Tyr Asp Asn Asp Pro Leu Arg Glu Gly
1160                1165                 1170

Ile Lys Tyr Ala Lys Gln Ala Gly Trp Asp Thr Val Ser Lys Ala
1175                1180                 1185

Ile Val Gly Gly Ala Lys Phe Ile Gly Asn Ser Tyr Val Lys Ala
1190                1195                 1200

Gly Gln Asn Thr Leu Tyr Lys Met Arg Trp Asn Pro Ala His Pro
1205                1210                 1215

Gly Thr His Gln Tyr Ala Thr Asp Val Asp Trp Ala Asn Ile Asn
1220                1225                 1230

Ala Lys Ile Ile Lys Gly Tyr Tyr Asp Lys Ile Gly Glu Val Gly
1235                1240                 1245

Lys Tyr Phe Asp Ile Pro Gln Tyr Lys
1250                1255

<210> SEQ ID NO 18
<211> LENGTH: 451
<212> TYPE: PRT
<213> ORGANISM: Staphylococcus aureus

<400> SEQUENCE: 18

Met Lys Asp Glu Gln Leu Tyr Tyr Phe Glu Lys Ser Pro Val Phe Lys
1               5                   10                  15

Ala Met Met His Phe Ser Leu Pro Met Met Ile Gly Thr Leu Leu Ser
                20                  25                  30

Val Ile Tyr Gly Ile Leu Asn Ile Tyr Phe Ile Gly Phe Leu Glu Asp
            35                  40                  45

Ser His Met Ile Ser Ala Ile Ser Leu Thr Leu Pro Val Phe Ala Ile
        50                  55                  60

Leu Met Gly Leu Gly Asn Leu Phe Gly Val Gly Ala Gly Thr Tyr Ile
65                  70                  75                  80

Ser Arg Leu Leu Gly Ala Lys Asp Tyr Ser Lys Ser Lys Phe Val Ser
                85                  90                  95

Ser Phe Ser Ile Tyr Gly Gly Ile Ala Leu Gly Leu Ile Val Ile Leu
            100                 105                 110

Val Thr Leu Pro Phe Ser Asp Gln Ile Ala Ala Ile Leu Gly Ala Arg
        115                 120                 125

Gly Glu Thr Leu Ala Leu Thr Ser Asn Tyr Leu Lys Val Met Phe Leu
    130                 135                 140

Ser Ala Pro Phe Val Ile Leu Phe Ile Leu Glu Gln Phe Ala Arg
145                 150                 155                 160

Ala Ile Gly Ala Pro Met Val Ser Met Ile Gly Met Leu Ala Ser Val
                165                 170                 175

Gly Leu Asn Ile Ile Leu Asp Pro Ile Leu Ile Phe Gly Phe Asp Leu
            180                 185                 190

Asn Val Val Gly Ala Ala Leu Gly Thr Ala Ile Ser Asn Val Ala Ala
        195                 200                 205

```
Ala Leu Phe Phe Ile Ile Tyr Phe Met Lys Asn Ser Asp Val Val Ser
    210                 215                 220

Val Asn Ile Lys Leu Ala Lys Pro Asn Lys Glu Met Leu Ser Glu Ile
225                 230                 235                 240

Phe Lys Ile Gly Ile Pro Ala Phe Leu Met Ser Ile Leu Met Gly Phe
                245                 250                 255

Thr Gly Leu Val Leu Asn Leu Phe Leu Ala His Tyr Gly Asn Phe Ala
                260                 265                 270

Ile Ala Ser Tyr Gly Ile Ser Phe Arg Leu Val Gln Phe Pro Glu Leu
            275                 280                 285

Ile Ile Met Gly Leu Cys Glu Gly Val Val Pro Leu Ile Ala Tyr Asn
        290                 295                 300

Phe Met Ala Asn Lys Gly Arg Met Lys Asp Val Ile Lys Ala Val Ile
305                 310                 315                 320

Met Ser Ile Gly Val Ile Phe Val Val Cys Met Ser Ala Val Phe Thr
                325                 330                 335

Ile Gly His His Met Val Gly Leu Phe Thr Thr Asp Gln Ala Ile Val
                340                 345                 350

Glu Met Ala Thr Phe Ile Leu Lys Val Thr Met Ala Ser Leu Leu Leu
            355                 360                 365

Asn Gly Ile Gly Phe Leu Phe Thr Gly Met Leu Gln Ala Thr Gly Gln
        370                 375                 380

Gly Arg Gly Ala Thr Ile Met Ala Ile Leu Gln Gly Ala Ile Ile Ile
385                 390                 395                 400

Pro Val Leu Phe Ile Met Asn Ala Leu Phe Gly Leu Thr Gly Val Ile
                405                 410                 415

Trp Ser Leu Leu Ile Ala Glu Ser Leu Cys Ala Leu Ala Ala Met Leu
                420                 425                 430

Ile Val Tyr Leu Leu Arg Asp Arg Leu Thr Val Asp Thr Ser Glu Leu
            435                 440                 445

Ile Glu Gly
    450

<210> SEQ ID NO 19
<211> LENGTH: 2066
<212> TYPE: PRT
<213> ORGANISM: Staphylococcus aureus

<400> SEQUENCE: 19

Met Asn Glu Lys Val Glu Gly Met Thr Leu Glu Leu Lys Leu Asp His
1               5                   10                  15

Leu Gly Val Gln Glu Gly Met Lys Gly Leu Lys Arg Gln Leu Gly Val
                20                  25                  30

Val Asn Ser Glu Met Lys Ala Asn Leu Ser Ala Phe Asp Lys Ser Glu
            35                  40                  45

Lys Ser Met Glu Lys Tyr Gln Ala Arg Ile Lys Gly Leu Asn Asp Arg
        50                  55                  60

Leu Lys Val Gln Lys Lys Met Tyr Ser Gln Val Glu Asp Glu Leu Lys
65                  70                  75                  80

Gln Val Asn Ala Asn Tyr Gln Lys Ala Lys Ser Ser Val Lys Asp Val
                85                  90                  95

Glu Lys Ala Tyr Leu Lys Leu Val Glu Ala Asn Lys Lys Glu Lys Leu
                100                 105                 110

Ala Leu Asp Lys Ser Lys Glu Ala Leu Lys Ser Ser Asn Thr Glu Leu
```

```
                115                 120                 125
Lys Lys Ala Glu Asn Gln Tyr Lys Arg Thr Asn Gln Arg Lys Gln Asp
            130                 135                 140

Ala Tyr Gln Lys Leu Lys Gln Leu Arg Asp Ala Glu Gln Lys Leu Lys
145                 150                 155                 160

Asn Ser Asn Gln Ala Thr Thr Ala Gln Leu Lys Arg Ala Ser Asp Ala
                165                 170                 175

Val Gln Lys Gln Ser Ala Lys His Lys Ala Leu Val Glu Gln Tyr Lys
                180                 185                 190

Gln Glu Gly Asn Gln Val Gln Lys Leu Lys Val Gln Asn Asp Asn Leu
                195                 200                 205

Ser Lys Ser Asn Asp Lys Ile Glu Ser Ser Tyr Ala Lys Thr Asn Thr
            210                 215                 220

Lys Leu Lys Gln Thr Glu Lys Glu Phe Asn Asp Leu Asn Asn Thr Ile
225                 230                 235                 240

Lys Asn His Ser Ala Asn Val Ala Lys Ala Glu Thr Ala Val Asn Lys
                245                 250                 255

Glu Lys Ala Ala Leu Asn Asn Leu Glu Arg Ser Ile Asp Lys Ala Ser
            260                 265                 270

Ser Glu Met Lys Thr Phe Asn Lys Glu Gln Met Ile Ala Gln Ser His
            275                 280                 285

Phe Gly Lys Leu Ala Ser Gln Ala Asp Val Met Ser Lys Lys Phe Ser
290                 295                 300

Ser Ile Gly Asp Lys Met Thr Ser Leu Gly Arg Thr Met Thr Met Gly
305                 310                 315                 320

Val Ser Thr Pro Ile Thr Leu Gly Leu Gly Ala Ala Leu Lys Thr Ser
                325                 330                 335

Ala Asp Phe Glu Gly Gln Met Ser Arg Val Gly Ala Ile Ala Gln Ala
            340                 345                 350

Ser Ser Lys Asp Leu Lys Ser Met Ser Asn Gln Ala Val Asp Leu Gly
            355                 360                 365

Ala Lys Thr Ser Lys Ser Ala Asn Glu Val Ala Lys Gly Met Glu Glu
            370                 375                 380

Leu Ala Ala Leu Gly Phe Asn Ala Lys Gln Thr Met Glu Ala Met Pro
385                 390                 395                 400

Gly Val Ile Ser Ala Ala Glu Ala Ser Gly Ala Glu Met Ala Thr Thr
                405                 410                 415

Ala Thr Val Met Ala Ser Ala Ile Asn Ser Phe Gly Leu Lys Ala Ser
                420                 425                 430

Asp Ala Asn His Val Ala Asp Leu Leu Ala Arg Ser Ala Asn Asp Ser
            435                 440                 445

Ala Ala Asp Ile Gln Tyr Met Gly Asp Ala Leu Lys Tyr Ala Gly Thr
            450                 455                 460

Pro Ala Lys Ala Leu Gly Val Ser Ile Glu Asp Thr Ser Ala Ala Ile
465                 470                 475                 480

Glu Val Leu Ser Asn Ser Gly Leu Glu Gly Ser Gln Ala Gly Thr Ala
                485                 490                 495

Leu Arg Ala Ser Phe Ile Arg Leu Ala Asn Pro Ser Lys Asn Thr Ala
            500                 505                 510

Lys Glu Met Lys Lys Leu Gly Ile His Leu Ser Asp Ala Lys Gly Gln
            515                 520                 525

Phe Val Gly Met Gly Glu Leu Ile Arg Gln Phe Gln Asp Asn Met Lys
            530                 535                 540
```

```
Gly Met Thr Arg Glu Gln Lys Leu Ala Thr Val Ala Thr Ile Val Gly
545                 550                 555                 560

Thr Glu Ala Ala Ser Gly Phe Leu Ala Leu Ile Glu Ala Gly Pro Asp
                565                 570                 575

Lys Ile Asn Ser Tyr Ser Lys Ser Leu Lys Asn Ser Asn Gly Glu Ser
            580                 585                 590

Lys Lys Ala Ala Asp Leu Met Lys Asp Asn Leu Lys Gly Ala Leu Glu
        595                 600                 605

Gln Leu Gly Gly Ala Phe Glu Ser Leu Ala Ile Glu Val Gly Lys Asp
610                 615                 620

Leu Thr Pro Met Ile Arg Ala Gly Ala Glu Gly Leu Thr Lys Leu Val
625                 630                 635                 640

Asp Gly Phe Thr His Leu Pro Gly Trp Val Arg Lys Ala Ser Val Gly
                645                 650                 655

Leu Ala Leu Phe Gly Ala Ile Gly Pro Ala Val Leu Ala Gly Gly
            660                 665                 670

Leu Leu Ile Arg Thr Val Gly Ser Ala Ala Lys Gly Tyr Ala Ser Leu
        675                 680                 685

Asn Arg Arg Ile Ala Glu Asn Thr Ile Leu Ser Asn Thr Asn Ser Lys
690                 695                 700

Ala Met Lys Ser Leu Gly Leu Gln Thr Leu Phe Leu Gly Ser Thr Thr
705                 710                 715                 720

Gly Lys Thr Ser Lys Gly Phe Lys Gly Leu Ala Gly Ala Met Met Phe
                725                 730                 735

Asn Leu Lys Pro Ile Asn Val Leu Lys Asn Ser Ala Lys Leu Ala Ile
            740                 745                 750

Leu Pro Phe Lys Leu Leu Lys Asn Gly Leu Gly Leu Ala Ala Lys Ser
        755                 760                 765

Leu Phe Ala Val Ser Gly Gly Ala Arg Phe Ala Gly Val Ala Leu Arg
770                 775                 780

Phe Leu Thr Gly Pro Ile Gly Ala Thr Ile Thr Ala Ile Thr Ile Ala
785                 790                 795                 800

Tyr Lys Val Phe Lys Thr Ala Tyr Asp Arg Val Glu Trp Phe Arg Asn
                805                 810                 815

Gly Ile Asn Gly Leu Gly Glu Thr Ile Lys Phe Phe Gly Gly Lys Ile
            820                 825                 830

Ile Gly Gly Ala Val Arg Lys Leu Gly Glu Phe Lys Asn Tyr Leu Gly
        835                 840                 845

Ser Ile Gly Lys Ser Phe Lys Glu Lys Phe Ser Lys Asp Met Lys Asp
850                 855                 860

Gly Tyr Lys Ser Leu Ser Asp Asp Leu Leu Lys Val Gly Val Asn
865                 870                 875                 880

Lys Phe Lys Gly Phe Met Gln Thr Met Gly Thr Ala Ser Lys Lys Ala
                885                 890                 895

Ser Asp Thr Val Lys Val Leu Gly Gly Val Ser Lys Glu Thr Glu
            900                 905                 910

Lys Ala Leu Glu Lys Tyr Val His Tyr Ser Glu Glu Asn Ser Arg Ile
        915                 920                 925

Met Glu Lys Val Arg Leu Asn Ser Gly Gln Ile Ser Glu Asp Lys Ala
930                 935                 940

Lys Lys Leu Leu Lys Ile Glu Thr Asp Leu Ser Asn Asn Leu Ile Ala
945                 950                 955                 960
```

```
Glu Ile Glu Lys Arg Asn Lys Lys Glu Leu Glu Lys Thr Gln Glu Leu
            965                 970                 975

Ile Asp Lys Tyr Ser Ala Phe Asp Glu Gln Glu Lys Gln Asn Ile Leu
            980                 985                 990

Thr Arg Thr Lys Glu Lys Asn Asp Leu Arg Ile Lys Lys Glu Gln Glu
            995                 1000                1005

Leu Asn Gln Lys Ile Lys Glu Leu Lys Glu Lys Ala Leu Ser Asp
        1010                1015                1020

Gly Gln Ile Ser Glu Asn Glu Arg Lys Glu Ile Glu Lys Leu Glu
        1025                1030                1035

Asn Gln Arg Arg Asp Ile Thr Val Lys Glu Leu Ser Lys Thr Glu
        1040                1045                1050

Lys Glu Gln Glu Arg Ile Leu Val Arg Met Gln Arg Asn Arg Asn
        1055                1060                1065

Ala Tyr Ser Ile Asp Glu Ala Ser Lys Ala Ile Lys Glu Ala Glu
        1070                1075                1080

Lys Ala Arg Lys Ala Arg Lys Lys Glu Val Asp Lys Gln Tyr Glu
        1085                1090                1095

Asp Asp Val Ile Ala Ile Lys Asn Asn Val Asn Leu Ser Lys Ser
        1100                1105                1110

Glu Lys Asp Lys Leu Leu Ala Ile Ala Asp Gln Arg His Lys Asp
        1115                1120                1125

Glu Val Arg Lys Ala Lys Ser Lys Lys Asp Ala Val Val Asp Val
        1130                1135                1140

Val Lys Lys Gln Asn Lys Asp Ile Asp Lys Glu Met Asp Leu Ser
        1145                1150                1155

Ser Gly Arg Val Tyr Lys Asn Thr Glu Lys Trp Trp Asn Gly Leu
        1160                1165                1170

Lys Ser Trp Trp Ser Asn Phe Arg Glu Asp Gln Lys Lys Lys Ser
        1175                1180                1185

Asp Lys Tyr Ala Lys Glu Gln Glu Glu Thr Ala Arg Arg Asn Arg
        1190                1195                1200

Glu Asn Ile Lys Lys Trp Phe Gly Asn Ala Trp Asp Gly Val Lys
        1205                1210                1215

Thr Lys Thr Gly Glu Ala Phe Ser Lys Met Gly Arg Asn Ala Asn
        1220                1225                1230

His Phe Gly Gly Glu Met Lys Lys Met Trp Ser Gly Ile Lys Gly
        1235                1240                1245

Ile Pro Ser Lys Leu Ser Ser Ser Trp Ser Ser Ala Lys Ser Ser
        1250                1255                1260

Val Gly Tyr His Thr Lys Ala Ile Ala Asn Ser Thr Gly Lys Trp
        1265                1270                1275

Phe Gly Lys Ala Trp Gln Ser Val Lys Ser Thr Thr Gly Ser Ile
        1280                1285                1290

Tyr Asn Gln Thr Lys Gln Lys Tyr Ser Asp Ala Ser Asp Lys Ala
        1295                1300                1305

Trp Ala His Ser Lys Ser Ile Trp Lys Gly Thr Ser Lys Trp Phe
        1310                1315                1320

Ser Asn Ala Tyr Lys Ser Ala Lys Gly Trp Leu Thr Asp Met Ala
        1325                1330                1335

Asn Lys Ser Arg Ser Lys Trp Asp Asn Ile Ser Ser Thr Ala Trp
        1340                1345                1350

Ser Asn Ala Lys Ser Val Trp Lys Gly Thr Ser Lys Trp Phe Gly
```

```
                1355                1360                1365
Asn Ser Tyr Lys Ser Leu Lys Gly Trp Thr Gly Asp Met Tyr Ser
    1370                1375                1380

Arg Ala His Asp Arg Phe Asp Ala Ile Ser Ser Ala Trp Ser
    1385                1390                1395

Asn Ala Lys Ser Val Phe Asn Gly Phe Arg Lys Trp Leu Ser Lys
    1400                1405                1410

Thr Tyr Asp Trp Ile Arg Asp Ile Gly Lys Asp Met Gly Arg Ala
    1415                1420                1425

Ala Ala Asp Leu Gly Lys Asn Val Ala Asn Lys Ala Ile Gly Gly
    1430                1435                1440

Leu Asn Ser Met Ile Gly Gly Ile Asn Lys Ile Ser Lys Ala Ile
    1445                1450                1455

Thr Asp Lys Asn Leu Ile Lys Pro Ile Pro Thr Leu Ser Thr Gly
    1460                1465                1470

Thr Leu Ala Gly Lys Gly Val Ala Thr Asp Asn Ser Gly Ala Leu
    1475                1480                1485

Thr Gln Pro Thr Phe Ala Val Leu Asn Asp Arg Gly Ser Gly Asn
    1490                1495                1500

Ala Pro Gly Gly Gly Val Gln Glu Val Ile His Arg Ala Asp Gly
    1505                1510                1515

Thr Phe His Ala Pro Gln Gly Arg Asp Val Val Pro Leu Gly
    1520                1525                1530

Val Gly Asp Ser Val Ile Asn Ala Asn Asp Thr Leu Lys Leu Gln
    1535                1540                1545

Arg Met Gly Val Leu Pro Lys Phe His Gly Gly Thr Lys Lys Lys
    1550                1555                1560

Lys Trp Met Glu Gln Val Thr Glu Asn Leu Gly Lys Lys Ala Gly
    1565                1570                1575

Asp Phe Gly Ser Lys Ala Lys Asn Thr Ala His Asn Ile Lys Lys
    1580                1585                1590

Gly Ala Glu Glu Met Val Glu Ala Ala Gly Asp Lys Ile Lys Asp
    1595                1600                1605

Gly Ala Ser Trp Leu Gly Asp Lys Ile Gly Asp Val Trp Asp Tyr
    1610                1615                1620

Val Gln His Pro Gly Lys Leu Val Asn Lys Val Met Ser Gly Leu
    1625                1630                1635

Asn Ile Asn Phe Gly Gly Gly Ala Asn Ala Thr Val Lys Ile Ala
    1640                1645                1650

Lys Gly Ala Tyr Ser Leu Leu Lys Lys Lys Leu Val Asp Lys Val
    1655                1660                1665

Lys Ser Trp Phe Glu Asp Phe Gly Gly Gly Asp Gly Ser Tyr
    1670                1675                1680

Leu Phe Asp His Pro Ile Trp Gln Arg Phe Gly Ser Tyr Thr Gly
    1685                1690                1695

Gly Leu Asn Phe Asn Gly Gly Arg His Tyr Gly Ile Asp Phe Gly
    1700                1705                1710

Met Pro Thr Gly Thr Asn Ile Tyr Ala Val Lys Gly Gly Ile Ala
    1715                1720                1725

Asp Lys Val Trp Thr Asp Tyr Gly Gly Gly Asn Ser Ile Gln Ile
    1730                1735                1740

Lys Thr Gly Ala Asn Glu Trp Asn Trp Tyr Met His Leu Ser Lys
    1745                1750                1755
```

```
Gln Leu Ala Arg Gln Gly Gln Arg Ile Lys Ala Gly Gln Leu Ile
    1760                1765                1770
Gly Lys Ser Gly Ala Thr Gly Asn Phe Val Arg Gly Ala His Leu
    1775                1780                1785
His Phe Gln Leu Met Gln Gly Ser His Pro Gly Asn Asp Thr Ala
    1790                1795                1800
Lys Asp Pro Glu Lys Trp Leu Lys Ser Leu Lys Gly Ser Gly Val
    1805                1810                1815
Arg Ser Gly Ser Gly Val Asn Lys Ala Ala Ser Ala Trp Ala Gly
    1820                1825                1830
Asp Ile Arg Arg Ala Ala Lys Arg Met Gly Val Asn Val Thr Ser
    1835                1840                1845
Gly Asp Val Gly Asn Ile Ile Ser Leu Ile Gln His Glu Ser Gly
    1850                1855                1860
Gly Asn Ala Gly Ile Thr Gln Ser Ser Ser Leu Arg Asp Ile Asn
    1865                1870                1875
Val Leu Gln Gly Asn Pro Ala Lys Gly Leu Leu Gln Tyr Ile Pro
    1880                1885                1890
Gln Thr Phe Arg His Tyr Ala Val Arg Gly His Asn Asn Ile Tyr
    1895                1900                1905
Ser Gly Tyr Asp Gln Leu Leu Ala Phe Phe Asn Asn Arg Tyr Trp
    1910                1915                1920
Arg Ser Gln Phe Asn Pro Arg Gly Gly Trp Ser Pro Ser Gly Pro
    1925                1930                1935
Arg Arg Tyr Ala Asn Gly Gly Leu Ile Thr Lys His Gln Leu Ala
    1940                1945                1950
Glu Val Gly Glu Gly Asp Lys Gln Glu Met Val Ile Pro Leu Thr
    1955                1960                1965
Arg Arg Lys Arg Ala Ile Gln Leu Thr Glu Gln Val Met Arg Ile
    1970                1975                1980
Ile Gly Met Asp Gly Lys Pro Asn Asn Ile Thr Val Asn Asn Asp
    1985                1990                1995
Thr Ser Thr Val Glu Lys Leu Leu Lys Gln Ile Val Met Leu Ser
    2000                2005                2010
Asp Lys Gly Asn Lys Leu Thr Asp Ala Leu Ile Gln Thr Val Ser
    2015                2020                2025
Ser Gln Asp Asn Asn Leu Gly Ser Asn Asp Ala Ile Arg Gly Leu
    2030                2035                2040
Glu Lys Ile Leu Ser Lys Gln Ser Gly His Arg Ala Asn Ala Asn
    2045                2050                2055
Asn Tyr Met Gly Gly Leu Thr Asn
    2060                2065

<210> SEQ ID NO 20
<211> LENGTH: 149
<212> TYPE: PRT
<213> ORGANISM: Staphylococcus aureus

<400> SEQUENCE: 20

Met Lys Lys Ser Lys Arg Leu Glu Ile Val Ser Thr Ile Val Lys Lys
1               5                   10                  15

His Lys Ile Tyr Lys Lys Glu Gln Ile Ile Ser Tyr Ile Glu Glu Tyr
            20                  25                  30

Phe Gly Val Arg Tyr Ser Ala Thr Thr Ile Ala Lys Asp Leu Lys Glu
```

```
                  35                  40                  45

Leu Asn Ile Tyr Arg Val Pro Ile Asp Cys Glu Thr Trp Ile Tyr Lys
 50                  55                  60

Ala Ile Asn Asn Gln Thr Glu Gln Glu Met Arg Glu Lys Phe Arg His
 65                  70                  75                  80

Tyr Cys Glu His Glu Val Leu Ser Ser Ile Asn Gly Ser Tyr Ile
                 85                  90                  95

Ile Val Lys Thr Ser Pro Gly Phe Ala Gln Gly Ile Asn Tyr Phe Ile
                100                 105                 110

Asp Gln Leu Asn Ile Glu Glu Ile Leu Gly Thr Val Ser Gly Asn Asp
                115                 120                 125

Thr Thr Leu Ile Leu Thr Ala Ser Asn Asp Met Ala Glu Tyr Val Tyr
                130                 135                 140

Ala Lys Leu Phe Lys
145

<210> SEQ ID NO 21
<211> LENGTH: 96
<212> TYPE: PRT
<213> ORGANISM: Staphylococcus aureus

<400> SEQUENCE: 21

Leu Phe Tyr Ala Cys His Phe Lys Val Lys Ile Gly Gly Val Ile Leu
 1               5                  10                  15

Thr Arg Thr Tyr Asn Ile Ile Gly Ile Leu Ser Cys Leu Ile Ser Phe
                 20                  25                  30

Ile Ile Met Ala Leu Pro Met Ile Trp Tyr Thr Ala Ser Ala Leu Trp
                 35                  40                  45

Phe Phe Pro Gly Ala Ile Met Ile Leu Leu Ser Leu Val Ile Val
 50                  55                  60

Phe Cys Tyr Ile Lys Thr Lys Asn Gln Leu His Leu Leu Ile Val
 65                  70                  75                  80

Leu Asn Ile Ile Ile Leu Leu Phe Phe Ser Leu Pro Leu Leu Leu Ser
                 85                  90                  95

<210> SEQ ID NO 22
<211> LENGTH: 86
<212> TYPE: PRT
<213> ORGANISM: Staphylococcus aureus

<400> SEQUENCE: 22

Leu Glu Tyr Asn Lys Lys Met Ile Asn Arg Ile His Arg Ile Gln Gly
 1               5                  10                  15

Gln Leu Asn Gly Val Ile Lys Met Met Glu Glu Glu Lys Asn Cys Lys
                 20                  25                  30

Asp Val Ile Ser Gln Leu Ser Ala Ser Lys Ser Ser Ile Gln Arg Leu
                 35                  40                  45

Met Gly Ile Ile Ile Ser Glu Asn Leu Val Glu Cys Val Lys Met Ser
 50                  55                  60

Glu Glu Asn Ser Glu Asp Ser Gln Ala Leu Ile Asn Glu Ala Val Glu
 65                  70                  75                  80

Leu Leu Ile Lys Ser Lys
                 85

<210> SEQ ID NO 23
<211> LENGTH: 466
<212> TYPE: PRT
```

-continued

<213> ORGANISM: Staphylococcus aureus

<400> SEQUENCE: 23

| | | | | | | | | | | | | | | |
|---|---|---|---|---|---|---|---|---|---|---|---|---|---|---|
| Met | Met | Lys | Arg | Lys | Pro | Thr | Phe | Leu | Glu | Ser | Ile | Ser | Thr | Met | Ile |
| 1 | | | | 5 | | | | | 10 | | | | | 15 | |
| Val | Met | Val | Ile | Val | Val | Thr | Gly | Phe | Val | Phe | Phe | Asp | Ile | Pro | |
| | | | 20 | | | | | 25 | | | | | 30 | | |
| Ile | Gln | Val | Leu | Leu | Ile | Ile | Ala | Ser | Ala | Tyr | Ala | Thr | Trp | Ile | Ala |
| | | 35 | | | | | 40 | | | | | 45 | | | |
| Lys | Arg | Val | Gly | Leu | Thr | Trp | Gln | Asp | Leu | Glu | Lys | Gly | Ile | Ala | Glu |
| | 50 | | | | | 55 | | | | | 60 | | | | |
| Arg | Leu | Asn | Thr | Ala | Met | Pro | Ala | Ile | Leu | Ile | Leu | Ala | Val | Gly |
| 65 | | | | | 70 | | | | | 75 | | | | | 80 |
| Ile | Ile | Val | Gly | Ser | Trp | Met | Phe | Ser | Gly | Thr | Val | Pro | Ala | Leu | Ile |
| | | | | 85 | | | | | 90 | | | | | 95 | |
| Tyr | Tyr | Gly | Leu | Asp | Leu | Leu | Asn | Pro | Ser | Tyr | Phe | Leu | Ile | Ser | Ala |
| | | | 100 | | | | | 105 | | | | | 110 | | |
| Phe | Phe | Ile | Ser | Ala | Val | Thr | Ser | Val | Ala | Thr | Gly | Thr | Ala | Trp | Gly |
| | | 115 | | | | | 120 | | | | | 125 | | | |
| Ser | Ala | Ser | Thr | Ala | Gly | Ile | Ala | Leu | Ile | Ser | Ile | Gly | Asn | Gln | Leu |
| | 130 | | | | | 135 | | | | | 140 | | | | |
| Gly | Ile | Pro | Pro | Gly | Met | Ala | Ala | Gly | Ala | Ile | Ile | Ala | Gly | Ala | Val |
| 145 | | | | | 150 | | | | | 155 | | | | | 160 |
| Phe | Gly | Asp | Lys | Met | Ser | Pro | Leu | Ser | Asp | Thr | Thr | Asn | Leu | Ala | Ala |
| | | | | 165 | | | | | 170 | | | | | 175 | |
| Leu | Val | Thr | Lys | Val | Asn | Ile | Phe | Lys | His | Ile | His | Ser | Met | Met | Trp |
| | | | 180 | | | | | 185 | | | | | 190 | | |
| Thr | Thr | Ile | Pro | Ala | Ser | Ile | Ile | Gly | Leu | Leu | Val | Trp | Phe | Ile | Ala |
| | | 195 | | | | | 200 | | | | | 205 | | | |
| Gly | Phe | Gln | Phe | Lys | Gly | His | Ser | Asn | Asp | Lys | Gln | Ile | Gln | Thr | Leu |
| | 210 | | | | | 215 | | | | | 220 | | | | |
| Leu | Ser | Glu | Leu | Ala | Gln | Ile | Tyr | Gln | Ile | Asn | Ile | Trp | Val | Trp | Val |
| 225 | | | | | 230 | | | | | 235 | | | | | 240 |
| Pro | Leu | Ile | Val | Ile | Ile | Val | Cys | Leu | Leu | Phe | Lys | Met | Ala | Thr | Val |
| | | | | 245 | | | | | 250 | | | | | 255 | |
| Pro | Ala | Met | Leu | Ile | Ser | Ser | Phe | Ser | Ala | Ile | Ile | Val | Gly | Thr | Phe |
| | | 260 | | | | | 265 | | | | | 270 | | | |
| Asn | His | His | Phe | Lys | Met | Thr | Asp | Gly | Phe | Lys | Ala | Thr | Phe | Ser | Gly |
| | 275 | | | | | 280 | | | | | 285 | | | | |
| Phe | Asn | Glu | Ser | Met | Ile | His | Gln | Ser | His | Ile | Ser | Ser | Ser | Val | Lys |
| 290 | | | | | 295 | | | | | 300 | | | | | |
| Ser | Leu | Leu | Glu | Gln | Gly | Gly | Met | Met | Ser | Met | Thr | Gln | Ile | Leu | Val |
| 305 | | | | | 310 | | | | | 315 | | | | | 320 |
| Thr | Ile | Phe | Cys | Gly | Tyr | Ala | Phe | Ala | Gly | Ile | Val | Glu | Lys | Ala | Gly |
| | | | | 325 | | | | | 330 | | | | | 335 | |
| Cys | Leu | Glu | Val | Leu | Leu | Thr | Thr | Ile | Ser | Lys | Gly | Ile | His | Ser | Val |
| | | | 340 | | | | | 345 | | | | | 350 | | |
| Gly | Ser | Leu | Ile | Cys | Ile | Thr | Val | Ile | Cys | Cys | Ile | Ala | Leu | Val | Phe |
| | | 355 | | | | | 360 | | | | | 365 | | | |
| Ala | Ala | Gly | Val | Ala | Ser | Ile | Val | Ile | Met | Val | Gly | Val | Leu | Met |
| | 370 | | | | | 375 | | | | | 380 | | | | |
| Lys | Asp | Leu | Phe | Glu | Lys | Tyr | Gln | Val | Ser | Arg | Ser | Val | Leu | Ser | Arg |
| 385 | | | | | 390 | | | | | 395 | | | | | 400 |

```
Thr Leu Glu Asp Ser Ser Thr Met Val Leu Pro Leu Ile Pro Trp Gly
            405                 410                 415

Thr Ser Gly Ile Tyr Tyr Thr Asn Gln Leu His Val Ser Val Glu Glu
        420                 425                 430

Phe Phe Ile Trp Thr Val Pro Cys Tyr Leu Cys Ala Ile Ile Ala Ile
            435                 440                 445

Ile Tyr Gly Phe Thr Gly Ile Gly Ile Lys Lys Ser Ser Asn Ser Arg
        450                 455                 460

Leu Thr
465

<210> SEQ ID NO 24
<211> LENGTH: 749
<212> TYPE: PRT
<213> ORGANISM: Staphylococcus aureus

<400> SEQUENCE: 24

Met Leu Glu Thr Asn Lys Asn His Ala Thr Ala Trp Gln Gly Phe Lys
1               5                   10                  15

Asn Gly Arg Trp Asn Arg His Val Asp Val Arg Glu Phe Ile Gln Leu
            20                  25                  30

Asn Tyr Thr Leu Tyr Glu Gly Asn Asp Ser Phe Leu Ala Gly Pro Thr
        35                  40                  45

Glu Ala Thr Ser Lys Leu Trp Glu Gln Val Met Gln Leu Ser Lys Glu
50                  55                  60

Glu Arg Glu Arg Gly Gly Met Trp Asp Met Asp Thr Lys Val Ala Ser
65                  70                  75                  80

Thr Ile Thr Ser His Asp Ala Gly Tyr Leu Asp Lys Asp Leu Glu Thr
                85                  90                  95

Ile Val Gly Val Gln Thr Glu Lys Pro Phe Lys Arg Ser Met Gln Pro
            100                 105                 110

Phe Gly Gly Ile Arg Met Ala Lys Ala Ala Cys Glu Ala Tyr Gly Tyr
        115                 120                 125

Glu Leu Asp Glu Glu Thr Glu Lys Ile Phe Thr Asp Tyr Arg Lys Thr
130                 135                 140

His Asn Gln Gly Val Phe Asp Ala Tyr Ser Arg Glu Met Leu Asn Cys
145                 150                 155                 160

Arg Lys Ala Gly Val Ile Thr Gly Leu Pro Asp Ala Tyr Gly Arg Gly
                165                 170                 175

Arg Ile Ile Gly Asp Tyr Arg Arg Val Ala Leu Tyr Gly Val Asp Phe
            180                 185                 190

Leu Met Glu Glu Lys Met His Asp Phe Asn Thr Met Ser Thr Glu Met
        195                 200                 205

Ser Glu Asp Val Ile Arg Leu Arg Glu Glu Leu Ser Glu Gln Tyr Arg
210                 215                 220

Ala Leu Lys Glu Leu Lys Glu Leu Gly Gln Lys Tyr Gly Phe Asp Leu
225                 230                 235                 240

Ser Arg Pro Ala Glu Asn Phe Lys Glu Ala Val Gln Trp Leu Tyr Leu
                245                 250                 255

Ala Tyr Leu Ala Ala Ile Lys Glu Gln Asn Gly Ala Ala Met Ser Leu
            260                 265                 270

Gly Arg Thr Ser Thr Phe Leu Asp Ile Tyr Ala Glu Arg Asp Leu Lys
        275                 280                 285

Ala Gly Val Ile Thr Glu Ser Glu Val Gln Glu Ile Ile Asp His Phe
290                 295                 300
```

```
Ile Met Lys Leu Arg Ile Val Lys Phe Ala Arg Thr Pro Asp Tyr Asn
305                 310                 315                 320

Glu Leu Phe Ser Gly Asp Pro Thr Trp Val Thr Glu Ser Ile Gly Gly
            325                 330                 335

Val Gly Ile Asp Gly Arg Pro Leu Val Thr Lys Asn Ser Phe Arg Phe
            340                 345                 350

Leu His Ser Leu Asp Asn Leu Gly Pro Ala Pro Glu Pro Asn Leu Thr
            355                 360                 365

Val Leu Trp Ser Val Arg Leu Pro Asp Asn Phe Lys Thr Tyr Cys Ala
370                 375                 380

Lys Met Ser Ile Lys Thr Ser Ile Gln Tyr Glu Asn Asp Asp Ile
385                 390                 395                 400

Met Arg Glu Ser Tyr Gly Asp Tyr Gly Ile Ala Cys Cys Val Ser
            405                 410                 415

Ala Met Thr Ile Gly Lys Gln Met Gln Phe Phe Gly Ala Arg Ala Asn
            420                 425                 430

Leu Ala Lys Thr Leu Leu Tyr Ala Ile Asn Gly Gly Lys Asp Glu Lys
            435                 440                 445

Ser Gly Ala Gln Val Gly Pro Asn Phe Glu Gly Ile Asn Ser Glu Val
450                 455                 460

Leu Glu Tyr Asp Glu Val Phe Lys Lys Phe Asp Gln Met Met Asp Trp
465                 470                 475                 480

Leu Ala Gly Val Tyr Ile Asn Ser Leu Asn Val Ile His Tyr Met His
            485                 490                 495

Asp Lys Tyr Ser Tyr Glu Arg Ile Glu Met Ala Leu His Asp Thr Glu
            500                 505                 510

Ile Val Arg Thr Met Ala Thr Gly Ile Ala Gly Leu Ser Val Ala Ala
            515                 520                 525

Asp Ser Leu Ser Ala Ile Lys Tyr Ala Gln Val Lys Pro Ile Arg Asn
530                 535                 540

Glu Glu Gly Leu Val Val Asp Phe Glu Ile Glu Gly Asp Phe Pro Lys
545                 550                 555                 560

Tyr Gly Asn Asn Asp Asp Arg Val Asp Asp Ile Ala Val Asp Leu Val
            565                 570                 575

Glu Arg Phe Met Thr Lys Leu Arg Ser His Lys Thr Tyr Arg Asp Ser
            580                 585                 590

Glu His Thr Met Ser Val Leu Thr Ile Thr Ser Asn Val Val Tyr Gly
            595                 600                 605

Lys Lys Thr Gly Asn Thr Pro Asp Gly Arg Lys Ala Gly Glu Pro Phe
610                 615                 620

Ala Pro Gly Ala Asn Pro Met His Gly Arg Asp Gln Lys Gly Ala Leu
625                 630                 635                 640

Ser Ser Leu Ser Ser Val Ala Lys Ile Pro Tyr Asp Cys Cys Lys Asp
            645                 650                 655

Gly Ile Ser Asn Thr Phe Ser Ile Val Pro Lys Ser Leu Gly Lys Glu
            660                 665                 670

Pro Glu Asp Gln Asn Arg Asn Leu Thr Ser Met Leu Asp Gly Tyr Ala
            675                 680                 685

Met Gln Cys Gly His His Leu Asn Ile Asn Val Phe Asn Arg Glu Thr
            690                 695                 700

Leu Ile Asp Ala Met Glu His Pro Glu Glu Tyr Pro Gln Leu Thr Ile
705                 710                 715                 720
```

Arg Val Ser Gly Tyr Ala Val Asn Phe Ile Lys Leu Thr Arg Glu Gln
            725                 730                 735

Gln Leu Asp Val Ile Ser Arg Thr Phe His Glu Ser Met
            740                 745

<210> SEQ ID NO 25
<211> LENGTH: 116
<212> TYPE: PRT
<213> ORGANISM: Staphylococcus aureus

<400> SEQUENCE: 25

Leu His Leu Phe Ile Leu Ser Ser His Ile Phe Lys Ser Ile Thr Phe
1               5                   10                  15

Asp Cys Gly Lys Glu Phe Ser Asn Trp Lys Thr Ile Cys Asn Cys His
            20                  25                  30

Asp Ile Ser Ile Phe Phe Ala Asp Pro Gly Thr Pro Ser Gln Arg Gly
        35                  40                  45

Leu Asn Glu His Ser Asn Gly Ile Ile Arg Arg Ser Gly Leu Asp Lys
    50                  55                  60

Glu Leu Asp Phe Asn Leu Val Thr Asp Asp His Ile Ile Ser Val Ala
65                  70                  75                  80

Gln Lys Ile Asn His His Pro Arg Lys Ser Leu Gly Tyr Arg Thr Pro
                85                  90                  95

Leu Glu Val Phe Met Ser Phe Ile Glu Asp Asp Lys Leu Val Gln Leu
            100                 105                 110

Asn Leu Thr Ile
        115

<210> SEQ ID NO 26
<211> LENGTH: 230
<212> TYPE: PRT
<213> ORGANISM: Staphylococcus aureus

<400> SEQUENCE: 26

Met Tyr Ser Ile Lys Met Arg Ser Ser Asn Gln Asp Val His Ile Ser
1               5                   10                  15

Gly Ala Glu Thr Ile Cys Glu Phe Asp Lys Ile Glu Gln Thr Val Gln
            20                  25                  30

Arg Phe Tyr Asn Lys Gly Phe Phe His Glu Asn Gly Gln Pro Asp Phe
        35                  40                  45

Leu Asn Ile Lys Ile Gln Lys Ile Met Glu Pro Ile Gln Gln Ile Lys
    50                  55                  60

Ala Leu Gln Ile Ile Glu Asp Asp Lys Ala Asn Leu Gln His Leu Thr
65                  70                  75                  80

Gln Glu Cys Gly Val Thr Glu Gln Ala Leu Asn Gln Gly Met Thr Tyr
                85                  90                  95

Ile Lys Asn Glu Thr Val Tyr Thr Gly Ala Ile Ile Leu Ser Ala Ile
            100                 105                 110

Ser Gly Lys Arg Leu Asp Ser Phe Gly Gln Arg Gly Ile Arg Ala Thr
        115                 120                 125

His Phe Ser Phe Glu Asp Ile Asn Asn Lys Gly Asp Leu Asn Glu Arg
    130                 135                 140

Val Thr Asp Ala Leu Ala Ile Ala Ser Cys Ile Asn Ala His Pro Tyr
145                 150                 155                 160

Val Lys Gly Glu Leu Cys Val Ser Asp Asp Leu Thr Tyr Thr Thr Gly
                165                 170                 175

```
Tyr Phe Ala Ala Ala Lys Ile Gly Tyr His Arg Leu Phe Asp Ile Lys
                180                 185                 190

Pro Val Asn Thr Arg Tyr Gly Gly Arg Ile Ile Phe Val Asp Asp Cys
            195                 200                 205

Ile Asp Leu Asn His Tyr Ile Ser Phe Leu Glu Ser Thr Pro Lys Gln
        210                 215                 220

Val Val Tyr Glu Thr Val
225                 230

<210> SEQ ID NO 27
<211> LENGTH: 518
<212> TYPE: PRT
<213> ORGANISM: Staphylococcus aureus

<400> SEQUENCE: 27

Val Glu Asn Thr Ile Asn Glu Ser Glu Lys Lys Arg Phe Lys Leu
1               5                   10                  15

Lys Met Pro Gly Ala Phe Met Ile Leu Phe Ile Leu Thr Val Val Ala
            20                  25                  30

Val Ile Ala Thr Trp Val Ile Pro Ala Gly Ala Tyr Ser Lys Leu Ser
        35                  40                  45

Tyr Glu Pro Ser Ser Gln Glu Leu Lys Ile Val Asn Pro His Asn Gln
    50                  55                  60

Val Lys Lys Val Pro Gly Thr Gln Gln Glu Leu Asp Lys Met Gly Val
65                  70                  75                  80

Lys Ile Lys Ile Glu Gln Phe Lys Ser Gly Ala Ile Asn Lys Pro Val
                85                  90                  95

Ser Ile Pro Asn Thr Tyr Glu Arg Leu Lys Gln His Pro Ala Gly Pro
            100                 105                 110

Glu Gln Ile Thr Ser Ser Met Val Glu Gly Thr Ile Glu Ala Val Asp
        115                 120                 125

Ile Met Val Phe Ile Leu Val Leu Gly Gly Leu Ile Gly Val Val Gln
    130                 135                 140

Ala Ser Gly Ser Phe Glu Ser Gly Leu Leu Ala Leu Thr Lys Lys Thr
145                 150                 155                 160

Lys Gly His Glu Phe Met Leu Ile Val Phe Val Ser Ile Leu Met Ile
                165                 170                 175

Ile Gly Gly Thr Leu Cys Gly Ile Glu Glu Ala Val Ala Phe Tyr
            180                 185                 190

Pro Ile Leu Val Pro Ile Phe Ile Ala Leu Gly Tyr Asp Ser Ile Val
        195                 200                 205

Ser Val Gly Ala Ile Phe Leu Ala Ser Ser Val Gly Ser Thr Phe Ser
    210                 215                 220

Thr Ile Asn Pro Phe Ser Val Val Ile Ala Ser Asn Ala Ala Gly Thr
225                 230                 235                 240

Thr Phe Thr Asp Gly Leu Tyr Trp Arg Ile Gly Ala Cys Ile Val Gly
                245                 250                 255

Ala Ile Phe Val Ile Ser Tyr Leu Tyr Trp Tyr Cys Lys Lys Ile Lys
            260                 265                 270

Asn Asp Pro Lys Ala Ser Tyr Ser Tyr Glu Lys Asp Ala Phe Glu
        275                 280                 285

Gln Gln Trp Ser Val Leu Lys Asp Asp Ser Ala His Phe Thr Leu
    290                 295                 300

Arg Lys Lys Ile Ile Leu Thr Leu Phe Val Leu Pro Phe Pro Ile Met
305                 310                 315                 320
```

Val Trp Gly Val Met Thr Gln Gly Trp Trp Phe Pro Val Met Ala Ser
            325                 330                 335

Ala Phe Leu Ile Phe Thr Ile Ile Ile Met Phe Ile Ala Gly Thr Gly
            340                 345                 350

Lys Ser Gly Leu Gly Glu Lys Gly Thr Val Asp Ala Phe Val Asn Gly
            355                 360                 365

Ala Ser Ser Leu Val Gly Val Ser Leu Ile Ile Gly Leu Ala Arg Gly
            370                 375                 380

Ile Asn Leu Val Leu Asn Glu Gly Met Ile Ser Asp Thr Ile Leu His
385                 390                 395                 400

Phe Ser Ser Leu Val Gln His Met Ser Gly Pro Leu Phe Ile Ile
            405                 410                 415

Val Leu Leu Phe Ile Phe Phe Cys Leu Gly Phe Ile Val Pro Ser Ser
            420                 425                 430

Ser Gly Leu Ala Val Leu Ser Met Pro Ile Phe Ala Pro Leu Ala Asp
            435                 440                 445

Thr Val Gly Ile Pro Arg Phe Val Ile Val Thr Thr Tyr Gln Phe Gly
            450                 455                 460

Gln Tyr Ala Met Leu Phe Leu Ala Pro Thr Gly Leu Val Met Ala Thr
465                 470                 475                 480

Leu Gln Met Leu Asn Met Arg Tyr Ser His Trp Phe Arg Phe Val Trp
            485                 490                 495

Pro Val Ala Phe Val Leu Ile Phe Gly Gly Val Leu Ile Thr
            500                 505                 510

Gln Val Leu Ile Tyr Ser
            515

<210> SEQ ID NO 28
<211> LENGTH: 283
<212> TYPE: PRT
<213> ORGANISM: Staphylococcus aureus

<400> SEQUENCE: 28

Met Ser Lys Ile Phe Val Thr Gly Ala Thr Gly Leu Ile Gly Ile Lys
1               5                   10                  15

Leu Val Gln Arg Leu Lys Glu Glu Gly His Glu Val Ala Gly Phe Thr
            20                  25                  30

Thr Ser Glu Asn Gly Gln Gln Lys Leu Ala Ala Val Asn Val Lys Ala
            35                  40                  45

Tyr Ile Gly Asp Ile Leu Lys Ala Asp Thr Ile Asp Gln Ala Leu Ala
            50                  55                  60

Asp Phe Lys Pro Glu Ile Ile Asn Gln Ile Thr Asp Leu Lys Asn
65                  70                  75                  80

Val Asp Met Ala Ala Asn Thr Lys Val Arg Ile Glu Gly Ser Lys Asn
            85                  90                  95

Leu Ile Asp Ala Ala Lys Lys His Asp Val Lys Lys Val Ile Ala Gln
            100                 105                 110

Ser Ile Ala Phe Met Tyr Glu Pro Gly Glu Gly Leu Ala Asn Glu Glu
            115                 120                 125

Thr Ser Leu Asp Phe Asn Ser Thr Gly Asp Arg Lys Val Thr Val Asp
            130                 135                 140

Gly Val Val Gly Leu Glu Glu Glu Thr Ala Arg Met Asp Glu Tyr Val
145                 150                 155                 160

Val Leu Arg Phe Gly Trp Leu Tyr Gly Pro Gly Thr Trp Tyr Gly Lys

```
                165                 170                 175
Asp Gly Met Ile Tyr Asn Gln Phe Met Asp Gly Gln Val Thr Leu Ser
            180                 185                 190

Asp Gly Val Thr Ser Phe Val His Leu Asp Asp Ala Val Glu Thr Ser
        195                 200                 205

Ile Gln Ala Ile His Phe Glu Asn Gly Ile Tyr Asn Val Ala Asp Asp
    210                 215                 220

Ala Pro Val Lys Gly Ser Glu Phe Ala Glu Trp Tyr Lys Glu Gln Leu
225                 230                 235                 240

Gly Val Glu Pro Asn Ile Asp Ile Gln Pro Ala Gln Pro Phe Glu Arg
                245                 250                 255

Gly Val Ser Asn Glu Lys Phe Lys Ala Gln Gly Gly Thr Leu Ile Tyr
            260                 265                 270

Gln Thr Trp Lys Asp Gly Met Asn Pro Ile Lys
        275                 280

<210> SEQ ID NO 29
<211> LENGTH: 54
<212> TYPE: PRT
<213> ORGANISM: Staphylococcus aureus

<400> SEQUENCE: 29

Met Pro Lys Leu Ile Ser Pro Thr Phe Glu Asp Ile Lys Thr Trp Tyr
1               5                   10                  15

Gln Leu Lys Glu Tyr Ser Lys Glu Asp Ile Ala Trp Tyr Val Asp Met
            20                  25                  30

Glu Val Ile Asp Lys Glu Tyr Ala Ile Ile Thr Gly Glu Lys Tyr
        35                  40                  45

Pro Glu Asn Leu Glu Ser
    50

<210> SEQ ID NO 30
<211> LENGTH: 250
<212> TYPE: PRT
<213> ORGANISM: Staphylococcus aureus

<400> SEQUENCE: 30

Met Ser Gln Ala Ala Glu Thr Leu Asp Gly Trp Tyr Ser Leu His Leu
1               5                   10                  15

Phe Tyr Ala Val Asp Trp Ala Ser Leu Arg Ile Val Pro Lys Asp Glu
            20                  25                  30

Arg Asp Ala Leu Val Thr Glu Phe Gln Ser Phe Leu Glu Asn Thr Ala
        35                  40                  45

Thr Val Arg Ser Ser Lys Ser Gly Asp Gln Ala Ile Tyr Asn Ile Thr
    50                  55                  60

Gly Gln Lys Ala Asp Leu Leu Leu Trp Phe Leu Arg Pro Glu Met Lys
65                  70                  75                  80

Ser Leu Asn His Ile Glu Asn Glu Phe Asn Lys Leu Arg Ile Ala Asp
                85                  90                  95

Phe Leu Ile Pro Thr Tyr Ser Tyr Val Ser Val Ile Glu Leu Ser Asn
            100                 105                 110

Tyr Leu Ala Gly Lys Ser Asp Glu Asp Pro Tyr Glu Asn Pro His Ile
        115                 120                 125

Lys Ala Arg Leu Tyr Pro Glu Leu Pro His Ser Asp Tyr Ile Cys Phe
    130                 135                 140

Tyr Pro Met Asn Lys Arg Arg Asn Glu Thr Tyr Asn Trp Tyr Met Leu
```

```
            145                 150                 155                 160
Thr Met Glu Glu Arg Gln Lys Leu Met Tyr Asp His Gly Met Ile Gly
                    165                 170                 175

Arg Lys Tyr Ala Gly Lys Ile Lys Gln Phe Ile Thr Gly Ser Val Gly
                180                 185                 190

Phe Asp Asp Phe Glu Trp Gly Val Thr Leu Phe Ser Asp Asp Val Leu
            195                 200                 205

Gln Phe Lys Lys Ile Val Tyr Glu Met Arg Phe Asp Glu Thr Thr Ala
        210                 215                 220

Arg Tyr Gly Glu Phe Gly Ser Phe Phe Val Gly His Leu Ile Asn Thr
225                 230                 235                 240

Asn Glu Phe Asp Gln Phe Phe Ala Ile Ser
                245                 250

<210> SEQ ID NO 31
<211> LENGTH: 244
<212> TYPE: PRT
<213> ORGANISM: Staphylococcus aureus

<400> SEQUENCE: 31

Val Asp Val Arg Phe Ile Asn Glu Gln Thr Ile Met Ile Tyr Phe Glu
1               5                   10                  15

Asn Lys Ile Ser Glu Glu Thr Tyr Arg Asn Val Thr Ala Met Val Arg
                20                  25                  30

Trp Ile Arg Glu Lys Glu Ile Leu Glu Ile Gln Asp Ile Val Pro Ser
            35                  40                  45

Tyr Arg Ala Val Leu Ile Tyr Phe Asp Glu Gln Ala Ile Thr Ser Ser
        50                  55                  60

Lys Leu Ile Glu Asn Leu Glu Leu Asn Lys Phe Asn Glu Lys Asn Val
65                  70                  75                  80

His Ala Val Asn Gln Thr Asn Arg Ile Ile Lys Ile Pro Val Gln Tyr
                85                  90                  95

Gly Gly Thr Tyr Gly Pro Asp Ile Glu Glu Val Ala Lys His Asn Arg
                100                 105                 110

Ile Thr Val Glu Gln Val Ile Glu Lys His Thr Ser Lys Pro Tyr Leu
            115                 120                 125

Ile Tyr Met Leu Gly Phe Met Pro Gly Phe Pro Tyr Leu Gly Gly Leu
        130                 135                 140

Asp Glu Gln Leu His Thr Pro Arg Arg Asn Gln Pro Arg Leu Lys Ile
145                 150                 155                 160

His Ala Gly Ser Val Gly Ile Ala Asn Asn Gln Thr Gly Leu Tyr Pro
                165                 170                 175

Ser Asp Ser Pro Gly Gly Trp Gln Ile Ile Gly Arg Thr Pro Leu Lys
            180                 185                 190

Val Phe Ser Ser Glu Arg Glu Pro Met Ser Met Tyr Glu Ala Gly Glu
        195                 200                 205

Trp Ile Gln Phe Tyr Ala Ile Asp Glu Gln Lys Phe Ile Gln Ile Glu
    210                 215                 220

Arg Asp Ile Ser Asp Gly Asn Phe Asn Val Asp Asp Trp Val Val Ile
225                 230                 235                 240

Glu Asn Val Asn

<210> SEQ ID NO 32
<211> LENGTH: 108
<212> TYPE: PRT
```

<213> ORGANISM: Staphylococcus aureus

<400> SEQUENCE: 32

Ile Tyr Tyr Arg Gly Ala His Tyr Met Lys Val Thr Asp Val Arg Leu
1               5                   10                  15

Arg Lys Ile Gln Thr Asp Gly Arg Met Lys Ala Leu Val Ser Ile Thr
            20                  25                  30

Leu Asp Glu Ala Phe Val Ile His Asp Leu Arg Val Ile Glu Gly Asn
        35                  40                  45

Ser Gly Leu Phe Val Ala Met Pro Ser Lys Arg Thr Pro Asp Gly Glu
    50                  55                  60

Phe Arg Asp Ile Ala His Pro Ile Asn Ser Asp Met Arg Gln Glu Ile
65                  70                  75                  80

Gln Asp Ala Val Met Lys Val Tyr Asp Glu Thr Asp Glu Val Val Pro
                85                  90                  95

Asp Lys Asn Ala Thr Ser Glu Asp Ser Glu Glu Ala
            100                 105

<210> SEQ ID NO 33
<211> LENGTH: 645
<212> TYPE: PRT
<213> ORGANISM: Staphylococcus aureus

<400> SEQUENCE: 33

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Glu Glu Thr Gly Gly Thr
        35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Ala Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
    130                 135                 140

Ala Pro Asn Ser Arg Pro Ile Asp Phe Glu Met Lys Lys Glu Asn Gly
145                 150                 155                 160

Glu Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
    210                 215                 220

Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe

```
                    245                 250                 255
        Ala Gln Pro Ile Tyr Asn Ser Ala Asp Lys Phe Lys Thr Glu Glu Asp
                        260                 265                 270

Tyr Lys Ala Glu Lys Leu Leu Ala Pro Tyr Lys Lys Ala Lys Thr Leu
                        275                 280                 285

Glu Arg Gln Val Tyr Glu Leu Asn Lys Ile Gln Asp Lys Leu Pro Glu
                        290                 295                 300

Lys Leu Lys Ala Glu Tyr Lys Lys Lys Leu Glu Asp Thr Lys Lys Ala
        305                 310                 315                 320

Leu Asp Glu Gln Val Lys Ser Ala Ile Thr Glu Phe Gln Asn Val Gln
                        325                 330                 335

Pro Thr Asn Glu Lys Met Thr Asp Leu Gln Asp Thr Lys Tyr Val Val
                        340                 345                 350

Tyr Glu Ser Val Glu Asn Asn Glu Ser Met Met Asp Thr Phe Val Lys
                        355                 360                 365

His Pro Ile Lys Thr Gly Met Leu Asn Gly Lys Lys Tyr Met Val Met
                        370                 375                 380

Glu Thr Thr Asn Asp Asp Tyr Trp Lys Asp Phe Met Val Glu Gly Gln
        385                 390                 395                 400

Arg Val Arg Thr Ile Ser Lys Asp Ala Lys Asn Asn Thr Arg Thr Ile
                        405                 410                 415

Ile Phe Pro Tyr Val Glu Gly Lys Thr Leu Tyr Asp Ala Ile Val Lys
                        420                 425                 430

Val His Val Lys Thr Ile Asp Tyr Asp Gly Gln Tyr His Val Arg Ile
                        435                 440                 445

Val Asp Lys Glu Ala Phe Thr Lys Ala Asn Thr Asp Lys Ser Asn Lys
                        450                 455                 460

Lys Glu Gln Gln Asp Asn Ser Ala Lys Lys Glu Ala Thr Pro Ala Thr
        465                 470                 475                 480

Pro Ser Lys Pro Thr Pro Ser Pro Val Glu Lys Glu Ser Gln Lys Gln
                        485                 490                 495

Asp Ser Gln Lys Asp Asp Asn Lys Gln Leu Pro Ser Val Glu Lys Glu
                        500                 505                 510

Asn Asp Ala Ser Ser Glu Ser Gly Lys Asp Lys Thr Pro Ala Thr Lys
                        515                 520                 525

Pro Thr Lys Gly Glu Val Glu Ser Ser Thr Thr Pro Thr Lys Val
                        530                 535                 540

Val Ser Thr Thr Gln Asn Val Ala Lys Pro Thr Thr Ala Ser Ser Lys
        545                 550                 555                 560

Thr Thr Lys Asp Val Val Gln Thr Ser Ala Gly Ser Ser Glu Ala Lys
                        565                 570                 575

Asp Ser Ala Pro Leu Gln Lys Ala Asn Ile Lys Asn Thr Asn Asp Gly
                        580                 585                 590

His Thr Gln Ser Gln Asn Asn Lys Asn Thr Gln Glu Asn Lys Ala Lys
                        595                 600                 605

Ser Leu Pro Gln Thr Gly Glu Glu Ser Asn Lys Asp Met Thr Leu Pro
                        610                 615                 620

Leu Met Ala Leu Leu Ala Leu Ser Ser Ile Val Ala Phe Val Leu Pro
        625                 630                 635                 640

Arg Lys Arg Lys Asn
                        645

<210> SEQ ID NO 34
```

```
<211> LENGTH: 476
<212> TYPE: PRT
<213> ORGANISM: Staphylococcus aureus

<400> SEQUENCE: 34

Met Lys Ser Asp Ser Leu Lys Glu Asn Ile Ile Tyr Gln Gly Leu Tyr
1               5                   10                  15

Gln Leu Ile Arg Thr Met Thr Pro Leu Ile Thr Ile Pro Ile Ile Ser
            20                  25                  30

Arg Ala Phe Gly Pro Ser Gly Val Gly Ile Val Ser Phe Ser Phe Asn
        35                  40                  45

Ile Val Gln Tyr Phe Leu Met Ile Ala Ser Val Gly Val Gln Leu Tyr
    50                  55                  60

Phe Asn Arg Val Ile Ala Lys Ser Val Asn Asp Lys Arg Gln Leu Ser
65                  70                  75                  80

Gln Gln Phe Trp Asp Ile Phe Val Ser Lys Leu Phe Leu Ala Leu Thr
                85                  90                  95

Val Phe Ala Met Tyr Met Val Val Ile Thr Ile Phe Ile Asp Asp Tyr
            100                 105                 110

Tyr Leu Ile Phe Leu Leu Gln Gly Ile Tyr Ile Gly Ala Ala Leu
            115                 120                 125

Asp Ile Ser Trp Phe Tyr Ala Gly Thr Glu Lys Phe Lys Ile Pro Ser
130                 135                 140

Leu Ser Asn Ile Val Ala Ser Gly Ile Val Leu Ser Val Val Val Ile
145                 150                 155                 160

Phe Val Lys Asp Gln Ser Asp Leu Ser Leu Tyr Val Phe Thr Ile Ala
                165                 170                 175

Ile Val Thr Val Leu Asn Gln Leu Pro Leu Phe Ile Tyr Leu Lys Arg
            180                 185                 190

Tyr Ile Ser Phe Val Ser Val Asn Trp Ile His Val Trp Gln Leu Phe
        195                 200                 205

Arg Ser Ser Leu Ala Tyr Leu Leu Pro Asn Gly Gln Leu Asn Leu Tyr
    210                 215                 220

Thr Ser Ile Ser Cys Val Val Leu Gly Leu Val Gly Thr Tyr Gln Gln
225                 230                 235                 240

Val Gly Ile Phe Ser Asn Ala Phe Asn Ile Leu Thr Val Ala Ile Ile
                245                 250                 255

Met Ile Asn Thr Phe Asp Leu Val Met Ile Pro Arg Ile Thr Lys Met
            260                 265                 270

Ser Ile Gln Gln Ser His Ser Leu Thr Lys Thr Leu Ala Asn Asn Met
        275                 280                 285

Asn Ile Gln Leu Ile Leu Thr Ile Pro Met Val Phe Gly Leu Ile Ala
    290                 295                 300

Ile Met Pro Ser Phe Tyr Leu Trp Phe Phe Gly Glu Glu Phe Ala Ser
305                 310                 315                 320

Thr Val Pro Leu Met Thr Ile Leu Ala Ile Leu Val Leu Ile Ile Pro
                325                 330                 335

Leu Asn Met Leu Ile Ser Arg Gln Tyr Leu Leu Ile Val Asn Lys Ile
            340                 345                 350

Arg Leu Tyr Asn Ala Ser Ile Thr Ile Gly Ala Val Met Asn Leu Val
        355                 360                 365

Leu Cys Leu Val Leu Ile Tyr Phe Tyr Gly Ile Tyr Gly Ala Ala Ile
    370                 375                 380

Ala Arg Leu Ile Thr Glu Phe Ile Leu Leu Ile Trp Arg Phe Val Asp
```

```
              385                 390                 395                 400
Ile Thr Lys Ile Asn Val Lys Leu Asn Ile Val Ser Thr Ile Gln Cys
                405                 410                 415
Val Ile Ala Ala Val Met Met Phe Ile Val Leu Gly Val Val Asn His
                420                 425                 430
Tyr Leu Pro Pro Thr Met Tyr Ala Thr Leu Leu Ile Ala Ile Gly
                435                 440                 445
Ile Val Val Tyr Leu Leu Met Met Thr Met Lys Asn Gln Tyr Val
                450                 455                 460
Trp Gln Ile Leu Arg His Leu Arg His Lys Thr Ile
465                 470                 475
```

<210> SEQ ID NO 35
<211> LENGTH: 409
<212> TYPE: PRT
<213> ORGANISM: Staphylococcus aureus

<400> SEQUENCE: 35

```
Met Gly Arg Asn Leu Lys Leu Lys Lys Glu Ser Asp Phe Glu Phe Thr
1                 5                   10                  15
Lys Asn His Lys Arg Leu Leu Leu Gly Ser Val Phe Leu Met Ala Thr
                20                  25                  30
Ser Ala Ile Gly Pro Ala Phe Leu Thr Gln Thr Ala Val Phe Thr Ser
                35                  40                  45
Gln Phe Phe Ala Ser Phe Ala Phe Ala Ile Leu Leu Ser Ile Ile Ile
                50                  55                  60
Asp Ile Gly Ala Gln Ile Asn Ile Trp Arg Ile Leu Val Val Thr Gly
65                  70                  75                  80
Leu Arg Gly Gln Glu Ile Ser Asn Lys Val Val Pro Gly Leu Gly Thr
                85                  90                  95
Val Ile Ser Ile Leu Ile Ala Phe Gly Gly Leu Ala Phe Asn Ile Gly
                100                 105                 110
Asn Ile Ala Gly Ala Gly Leu Gly Leu Asn Ala Ile Phe Gly Leu Asp
                115                 120                 125
Val Lys Trp Gly Ala Ala Ile Thr Ala Ile Phe Ala Ile Leu Ile Phe
                130                 135                 140
Val Ser Lys Ser Gly Gln Lys Ile Met Asp Val Val Ser Met Ile Leu
145                 150                 155                 160
Gly Ile Val Met Ile Leu Val Val Ala Tyr Val Met Phe Val Ser Asn
                165                 170                 175
Pro Pro Tyr Gly Asp Ala Phe Val His Thr Phe Ala Pro Glu His Pro
                180                 185                 190
Met Lys Leu Val Leu Pro Ile Ile Thr Leu Val Gly Gly Thr Val Gly
                195                 200                 205
Gly Tyr Ile Thr Phe Ala Gly Ala His Arg Ile Leu Asp Ser Gly Ile
                210                 215                 220
Lys Gly Lys Gln Tyr Leu Pro Phe Val Asn Gln Ser Ala Ile Ala Gly
225                 230                 235                 240
Ile Leu Thr Thr Gly Ile Met Arg Thr Leu Leu Phe Leu Ala Val Leu
                245                 250                 255
Gly Val Val Val Thr Gly Val Thr Leu Ser Ser Glu Asn Pro Pro Ala
                260                 265                 270
Ser Val Phe Glu His Ala Ile Gly Pro Ile Gly Lys Asn Ile Phe Gly
                275                 280                 285
```

```
Ile Val Leu Phe Ala Ala Met Ser Ser Val Ile Gly Ser Ala Tyr
    290                 295                 300

Thr Ser Ala Thr Phe Leu Lys Thr Leu His Lys Ser Leu Asn Glu Arg
305                 310                 315                 320

Ser Asn Leu Ile Val Ile Val Phe Ile Val Ser Thr Met Ile Phe
                325                 330                 335

Leu Phe Ile Gly Lys Pro Ile Ser Leu Leu Ile Ile Ala Gly Ala Ile
                340                 345                 350

Asn Gly Trp Ile Leu Pro Ile Thr Leu Gly Ala Ile Leu Ile Ala Ser
                355                 360                 365

Lys Lys Lys Ser Ile Val Gly Asp Tyr Lys His Pro Asn Trp Met Phe
370                 375                 380

Ile Phe Gly Ile Val Ala Val Leu Val Thr Ile Leu Thr Gly Ile Phe
385                 390                 395                 400

Ser Phe Lys Glu Val Leu Gln Leu Phe
                405
```

<210> SEQ ID NO 36
<211> LENGTH: 2481
<212> TYPE: PRT
<213> ORGANISM: Staphylococcus aureus

<400> SEQUENCE: 36

```
Met Asn Leu Phe Arg Gln Gln Lys Phe Ser Ile Arg Lys Phe Asn Val
1               5                   10                  15

Gly Ile Phe Ser Ala Leu Ile Ala Thr Val Thr Phe Ile Ser Thr Asn
                20                  25                  30

Pro Thr Thr Ala Ser Ala Ala Glu Gln Asn Gln Pro Ala Gln Asn Gln
                35                  40                  45

Pro Ala Gln Pro Ala Asp Ala Asn Thr Gln Pro Asn Ala Asn Ala Gly
50                  55                  60

Ala Gln Ala Asn Pro Ala Ala Gln Pro Ala Asn Gln Gly Gly Gln Ala
65                  70                  75                  80

Asn Pro Ala Gly Gly Ala Ala Gln Pro Ala Gly Gln Gly Asn Gln Ala
                85                  90                  95

Asp Pro Asn Asn Ala Ala Gln Ala Gln Pro Gly Asn Gln Ala Ala Pro
                100                 105                 110

Ala Asn Gln Ala Gly Gln Gly Asn Asn Gln Ala Thr Pro Asn Asn Asn
                115                 120                 125

Ala Thr Pro Ala Asn Gln Thr Gln Pro Ala Asn Ala Pro Ala Ala Ala
                130                 135                 140

Gln Pro Ala Ala Pro Val Ala Ala Asn Ala Gln Thr Gln Asp Pro Asn
145                 150                 155                 160

Ala Ser Asn Thr Gly Glu Gly Ser Ile Asn Thr Thr Leu Thr Phe Asp
                165                 170                 175

Asp Pro Ala Ile Ser Thr Asp Glu Asn Arg Gln Asp Pro Thr Val Thr
                180                 185                 190

Val Thr Asp Lys Val Asn Gly Tyr Ser Leu Ile Asn Asn Gly Lys Ile
                195                 200                 205

Gly Phe Val Asn Ser Glu Leu Arg Arg Ser Asp Met Phe Asp Lys Asn
                210                 215                 220

Asn Pro Gln Asn Tyr Gln Ala Lys Gly Asn Val Ala Ala Leu Gly Arg
225                 230                 235                 240

Val Asn Ala Asn Asp Ser Thr Asp His Gly Asn Phe Asn Gly Ile Thr
                245                 250                 255
```

```
Lys Thr Val Asn Val Lys Pro Asp Ser Glu Leu Ile Ile Asn Phe Thr
            260                 265                 270

Thr Met Gln Thr Asn Ser Lys Gln Gly Ala Thr Asn Leu Val Ile Lys
        275                 280                 285

Asp Ala Lys Lys Asn Thr Glu Leu Ala Thr Val Asn Val Ala Lys Thr
290                 295                 300

Gly Thr Ala His Leu Phe Lys Val Pro Thr Asp Ala Asp Arg Leu Asp
305                 310                 315                 320

Leu Gln Phe Ile Pro Asp Asn Thr Ala Val Ala Asp Ala Ser Arg Ile
                325                 330                 335

Thr Thr Asn Lys Asp Gly Tyr Lys Tyr Tyr Ser Phe Ile Asp Asn Val
            340                 345                 350

Gly Leu Phe Ser Gly Ser His Leu Tyr Val Lys Asn Arg Asp Leu Ala
        355                 360                 365

Pro Lys Ala Thr Asn Asn Lys Glu Tyr Thr Ile Asn Thr Glu Ile Gly
    370                 375                 380

Asn Asn Gly Asn Phe Gly Ala Ser Leu Lys Ala Asp Gln Phe Lys Tyr
385                 390                 395                 400

Glu Val Thr Leu Pro Gln Gly Val Thr Tyr Val Asn Asp Ser Leu Thr
                405                 410                 415

Thr Thr Phe Pro Asn Gly Asn Glu Asp Ser Thr Val Leu Lys Asn Met
            420                 425                 430

Thr Val Asn Tyr Asp Gln Thr Ala Asn Lys Val Thr Phe Thr Ser Gln
        435                 440                 445

Gly Val Thr Thr Ala Arg Gly Thr His Thr Lys Glu Val Leu Phe Pro
    450                 455                 460

Asp Lys Ser Leu Lys Leu Ser Tyr Lys Val Asn Val Ala Asn Ile Asp
465                 470                 475                 480

Thr Pro Lys Asn Ile Asp Phe Asn Glu Lys Leu Thr Tyr Arg Thr Ala
                485                 490                 495

Ser Asp Val Val Ile Asn Asn Ala Gln Pro Glu Val Thr Leu Thr Ala
            500                 505                 510

Asp Pro Phe Ser Val Ala Val Glu Met Asn Lys Asp Ala Leu Gln Gln
        515                 520                 525

Gln Val Asn Ser Gln Val Asp Asn Ser His Tyr Thr Thr Ala Ser Ile
    530                 535                 540

Ala Glu Tyr Asn Lys Leu Lys Gln Gln Ala Asp Thr Ile Leu Asn Glu
545                 550                 555                 560

Asp Ala Asn His Val Glu Thr Ala Asn Arg Ala Ser Gln Ala Asp Ile
                565                 570                 575

Asp Gly Leu Val Thr Lys Leu Gln Ala Ala Leu Ile Asp Asn Gln Ala
            580                 585                 590

Ala Ile Ala Glu Leu Asp Thr Lys Ala Gln Glu Lys Val Thr Ala Ala
        595                 600                 605

Gln Gln Ser Lys Lys Val Thr Gln Asp Glu Val Ala Ala Leu Val Thr
    610                 615                 620

Lys Ile Asn Asn Asp Lys Asn Asn Ala Ile Ala Glu Ile Asn Lys Gln
625                 630                 635                 640

Thr Thr Ser Gln Gly Val Thr Thr Glu Lys Asp Asn Gly Ile Ala Val
                645                 650                 655

Leu Glu Gln Asp Val Ile Thr Pro Thr Val Lys Pro Gln Ala Lys Gln
            660                 665                 670
```

-continued

```
Asp Ile Ile Gln Ala Val Thr Thr Arg Lys Gln Gln Ile Lys Lys Ser
            675                 680                 685

Asn Ala Ser Leu Gln Asp Glu Lys Asp Val Ala Asn Asp Lys Ile Gly
    690                 695                 700

Lys Ile Glu Thr Lys Ala Ile Lys Asp Ile Asp Ala Ala Thr Thr Asn
705                 710                 715                 720

Ala Gln Val Glu Ala Ile Lys Thr Lys Ala Ile Asn Asp Ile Asn Gln
                725                 730                 735

Thr Thr Pro Ala Thr Thr Ala Lys Ala Ala Leu Glu Glu Phe Asp
                740                 745                 750

Glu Val Val Gln Ala Gln Ile Asp Gln Ala Pro Leu Asn Pro Asp Thr
            755                 760                 765

Thr Asn Glu Glu Val Ala Glu Ala Ile Glu Arg Ile Asn Ala Ala Lys
    770                 775                 780

Val Ser Gly Val Lys Ala Ile Glu Ala Thr Thr Thr Ala Gln Asp Leu
785                 790                 795                 800

Glu Arg Val Lys Asn Glu Glu Ile Phe Lys Ile Glu Asn Ile Thr Asp
                805                 810                 815

Ser Thr Gln Thr Lys Met Asp Ala Tyr Lys Glu Val Arg Gln Ala Ala
            820                 825                 830

Thr Ala Arg Lys Ala Gln Asn Ala Thr Val Ser Asn Ala Thr Asp Glu
    835                 840                 845

Glu Val Ala Glu Ala Asn Ala Ala Val Asp Ala Ala Gln Thr Glu Gly
    850                 855                 860

Leu His Asp Ile Gln Val Val Lys Ser Gln Gln Glu Val Ala Asp Thr
865                 870                 875                 880

Lys Ala Lys Val Leu Asp Lys Ile Asn Ala Ile Gln Thr Gln Ala Lys
                885                 890                 895

Val Lys Pro Ala Ala Asp Thr Glu Val Glu Asn Ala Tyr Asn Thr Arg
            900                 905                 910

Lys Gln Glu Ile Gln Asn Ser Asn Ala Ser Thr Glu Glu Lys Glu
    915                 920                 925

Ala Ala Tyr Thr Glu Leu Asp Ala Lys Lys Gln Glu Ala Arg Thr Asn
    930                 935                 940

Leu Asp Ala Ala Asn Thr Asn Ser Asp Val Thr Thr Ala Lys Asp Asn
945                 950                 955                 960

Gly Ile Ala Ala Ile Asn Gln Val Gln Ala Ala Thr Thr Lys Lys Ser
                965                 970                 975

Asp Ala Lys Ala Glu Ile Ala Gln Lys Ala Ser Glu Arg Lys Thr Ala
            980                 985                 990

Ile Glu Ala Met Asn Asp Ser Thr  Thr Glu Glu Gln Gln  Ala Ala Lys
            995                1000                1005

Asp Lys Val Asp Gln Ala Val  Val Thr Ala Asn Ala  Asp Ile Asp
    1010                1015                1020

Asn Ala  Thr Ala Asn Thr Asp  Val Asp Asn Ala Lys  Thr Thr Asn
    1025                1030                1035

Glu Ala  Thr Ile Ala Ala Ile  Thr Pro Asp Ala Asn  Val Lys Pro
    1040                1045                1050

Ala Ala  Lys Gln Ala Ile Ala  Asp Lys Val Gln Ala  Gln Glu Thr
            1055                1060                1065

Ala Ile  Asp Ala Asn Asn Gly  Ser Thr Thr Glu Glu  Lys Glu Ala
            1070                1075                1080

Ala Lys  Gln Gln Val Gln Thr  Glu Lys Thr Ala Ala  Asp Ala Ala
```

-continued

```
            1085                1090                1095
Ile Asp Ala Ala His Ser Asn Val Glu Val Glu Ala Ala Lys Asn
            1100                1105                1110
Ala Glu Ile Ala Lys Ile Glu Ala Ile Gln Pro Ala Thr Thr Thr
            1115                1120                1125
Lys Asp Asn Ala Lys Gln Ala Ile Ala Thr Lys Ala Asn Glu Arg
            1130                1135                1140
Lys Thr Ala Ile Ala Gln Thr Gln Asp Ile Thr Ala Glu Glu Ile
            1145                1150                1155
Ala Ala Ala Asn Ala Asp Val Asp Asn Ala Val Thr Gln Ala Asn
            1160                1165                1170
Ser Asn Ile Glu Ala Ala Asn Ser Gln Asn Asp Val Asp Gln Ala
            1175                1180                1185
Lys Thr Thr Gly Glu Thr Ser Ile Asp Gln Val Thr Pro Thr Val
            1190                1195                1200
Asn Lys Lys Ala Thr Ala Arg Asn Glu Ile Thr Ala Ile Leu Asn
            1205                1210                1215
Asn Lys Leu Gln Glu Ile Gln Ala Thr Pro Asp Ala Thr Asp Glu
            1220                1225                1230
Glu Lys Gln Ala Ala Asp Ala Glu Ala Asn Thr Glu Asn Gly Lys
            1235                1240                1245
Ala Asn Gln Ala Ile Ser Ala Ala Thr Thr Asn Ala Gln Val Asp
            1250                1255                1260
Glu Ala Lys Ala Asn Ala Glu Ala Ala Ile Asn Ala Val Thr Pro
            1265                1270                1275
Lys Val Val Lys Gln Ala Ala Lys Asp Glu Ile Asp Gln Leu
            1280                1285                1290
Gln Ala Thr Gln Thr Asn Val Ile Asn Asn Asp Gln Asn Ala Thr
            1295                1300                1305
Asn Glu Glu Lys Glu Ala Ala Ile Gln Gln Leu Ala Thr Ala Val
            1310                1315                1320
Thr Asp Ala Lys Asn Asn Ile Thr Ala Ala Thr Asp Asp Asn Gly
            1325                1330                1335
Val Asp Thr Ala Lys Asp Ala Gly Lys Asn Ser Ile Gln Ser Thr
            1340                1345                1350
Gln Pro Ala Thr Ala Val Lys Ser Asn Ala Lys Asn Glu Val Asp
            1355                1360                1365
Gln Ala Val Thr Thr Gln Asn Gln Ala Ile Asp Asn Thr Thr Gly
            1370                1375                1380
Ala Thr Thr Glu Glu Lys Asn Ala Ala Lys Asp Leu Val Leu Lys
            1385                1390                1395
Ala Lys Glu Lys Ala Tyr Gln Asp Ile Leu Asn Ala Gln Thr Thr
            1400                1405                1410
Asn Asp Val Thr Gln Ile Lys Asp Gln Ala Val Ala Asp Ile Gln
            1415                1420                1425
Gly Ile Thr Ala Asp Thr Thr Ile Lys Asp Val Ala Lys Asp Glu
            1430                1435                1440
Leu Ala Thr Lys Ala Asn Glu Gln Lys Ala Leu Ile Ala Gln Thr
            1445                1450                1455
Ala Asp Ala Thr Thr Glu Glu Lys Glu Gln Ala Asn Gln Gln Val
            1460                1465                1470
Asp Ala Gln Leu Thr Gln Gly Asn Gln Asn Ile Glu Asn Ala Gln
            1475                1480                1485
```

-continued

```
Ser Ile Asp Asp Val Asn Thr Ala Lys Asp Asn Ala Ile Gln Ala
    1490            1495                1500

Ile Asp Pro Ile Gln Ala Ser Thr Asp Val Lys Thr Asn Ala Arg
    1505            1510                1515

Ala Glu Leu Leu Thr Glu Met Gln Asn Lys Ile Thr Glu Ile Leu
    1520            1525                1530

Asn Asn Asn Glu Thr Thr Asn Glu Glu Lys Gly Asn Asp Ile Gly
    1535            1540                1545

Pro Val Arg Ala Ala Tyr Glu Glu Gly Leu Asn Asn Ile Asn Ala
    1550            1555                1560

Ala Thr Thr Thr Gly Asp Val Thr Thr Ala Lys Asp Thr Ala Val
    1565            1570                1575

Gln Lys Val Gln Gln Leu His Ala Asn Pro Val Lys Lys Pro Ala
    1580            1585                1590

Gly Lys Lys Glu Leu Asp Gln Ala Ala Ala Asp Lys Lys Thr Gln
    1595            1600                1605

Ile Glu Gln Thr Pro Asn Ala Ser Gln Gln Glu Ile Asn Asp Ala
    1610            1615                1620

Lys Gln Glu Val Asp Thr Glu Leu Asn Gln Ala Lys Thr Asn Val
    1625            1630                1635

Asp Gln Ser Ser Thr Asn Glu Tyr Val Asp Asn Ala Val Lys Glu
    1640            1645                1650

Gly Lys Ala Lys Ile Asn Ala Val Lys Thr Phe Ser Glu Tyr Lys
    1655            1660                1665

Lys Asp Ala Leu Ala Lys Ile Glu Asp Ala Tyr Asn Ala Lys Val
    1670            1675                1680

Asn Glu Ala Asp Asn Ser Asn Ala Ser Thr Ser Ser Glu Ile Ala
    1685            1690                1695

Glu Ala Lys Gln Lys Leu Ala Glu Leu Lys Gln Thr Ala Asp Gln
    1700            1705                1710

Asn Val Asn Gln Ala Thr Ser Lys Asp Asp Ile Glu Val Gln Ile
    1715            1720                1725

His Asn Asp Leu Asp Asn Ile Asn Asp Tyr Thr Ile Pro Thr Gly
    1730            1735                1740

Lys Lys Glu Ser Ala Thr Thr Asp Leu Tyr Ala Tyr Ala Asp Gln
    1745            1750                1755

Lys Lys Asn Asn Ile Ser Ala Asp Thr Asn Ala Thr Gln Asp Glu
    1760            1765                1770

Lys Gln Gln Ala Ile Lys Gln Val Asp Gln Asn Val Gln Thr Ala
    1775            1780                1785

Leu Glu Asn Ile Asn Asn Gly Val Asp Asn Gly Asp Val Asp Asp
    1790            1795                1800

Ala Leu Thr Gln Gly Lys Ala Ala Ile Asp Thr Ile Gln Val Asp
    1805            1810                1815

Ala Thr Val Lys Pro Lys Ala Asn Gln Ala Ile Glu Ala Lys Ala
    1820            1825                1830

Glu Asp Thr Lys Glu Ser Ile Asp His Ser Asp Gln Leu Thr Ala
    1835            1840                1845

Glu Glu Lys Thr Glu Ala Leu Ala Met Ile Lys Gln Ile Thr Asp
    1850            1855                1860

Gln Ala Lys Gln Gly Ile Thr Asp Ala Thr Thr Thr Ala Glu Val
    1865            1870                1875
```

```
Glu Lys Ala Lys Ala Gln Gly Leu Glu Ala Phe Asp Asn Ile Gln
    1880            1885                1890

Ile Asp Ser Thr Glu Lys Gln Lys Ala Ile Glu Glu Leu Glu Thr
    1895            1900                1905

Ala Leu Asp Gln Ile Glu Ala Gly Val Asn Val Asp Ala Asp Ala
    1910            1915                1920

Thr Thr Glu Glu Lys Glu Ala Phe Thr Asn Ala Leu Glu Asp Ile
    1925            1930                1935

Leu Ser Lys Ala Thr Glu Asp Ile Ser Asp Gln Thr Thr Asn Ala
    1940            1945                1950

Glu Ile Ala Thr Val Lys Asn Ser Ala Leu Glu Gln Leu Lys Ala
    1955            1960                1965

Gln Arg Ile Asn Pro Val Val Lys Lys Asn Ala Leu Glu Ala Ile
    1970            1975                1980

Arg Glu Val Val Asn Lys Gln Ile Glu Ile Ile Lys Asn Ala Asp
    1985            1990                1995

Ala Asp Ala Ser Ala Lys Glu Ile Ala Arg Thr Asp Leu Gly Arg
    2000            2005                2010

Tyr Phe Asp Arg Phe Ala Asp Lys Leu Asp Lys Thr Gln Thr Asn
    2015            2020                2025

Thr Glu Val Ala Glu Leu Gln Asn Val Thr Ile Pro Ala Ile Glu
    2030            2035                2040

Ala Ile Val Pro Gln Asn Asp Pro Asp Ala Asn Asp Thr Asn Asn
    2045            2050                2055

Gly Thr Asp Asn Asp Ala Thr Ala Asn Ser Asn Ala Asn Ala
    2060            2065                2070

Thr Pro Glu Asn Thr Gly Gln Pro Asn Val Ser Glu Thr Thr Asp
    2075            2080                2085

Asn Gly Lys Ala Asp Ala Ser Pro Thr Thr Pro Asn Asn Ser Asp
    2090            2095                2100

Ala Ala Thr Gly Glu Thr Thr Val Thr Ser Ala Thr Asp Asp Ala
    2105            2110                2115

Lys Asp Lys Pro Gln Ala Asn Asn Asn Ser Ser Ala Asp Ala Ser
    2120            2125                2130

Thr Asn Ser Pro Thr Met Asp Asn Asp Val Thr Ser Lys Pro Glu
    2135            2140                2145

Val Glu Ser Thr Asn Asn Gly Thr Thr Asp Lys Pro Val Thr Glu
    2150            2155                2160

Thr Asp Asn Ala Thr Pro Ala Glu Ser Thr Thr Asn Asn Asn Ser
    2165            2170                2175

Thr Thr Thr Ala Thr Asn Glu Asn Ala Pro Thr Gly Ser Thr Ala
    2180            2185                2190

Thr Ala Pro Thr Thr Ala Ser Thr Glu Ala Ala Ser Ser Ala Asp
    2195            2200                2205

Ser Lys Asp Asn Ala Ser Val Asn Asp Ser Lys Gln Asn Ala Glu
    2210            2215                2220

Val Asn Asn Ser Ala Glu Ser Gln Ser Thr Asn Gly Lys Val Ala
    2225            2230                2235

Gln Pro Lys Ser Glu Asn Lys Ala Lys Ala Glu Lys Asp Gly Arg
    2240            2245                2250

Asp Ser Thr Asn Gln Ser Met Val Glu Ser Thr Thr Glu Thr Leu
    2255            2260                2265
```

-continued

```
Pro Ser Ala Asp Ile Thr Glu Pro Asn Val Pro Ser Asn Thr Ser
    2270                2275            2280

Lys Asp Lys Glu Glu Ser Thr Thr Asn Gln Thr Asp Ala Gly Gln
    2285                2290            2295

Leu Lys Ser Glu Thr Asn Val Ala Ser Asn Glu Ala Asp Lys Ser
    2300                2305            2310

Pro Ser Lys Ala Asp Thr Glu Val Ser Asn Lys Pro Ser Thr Ser
    2315                2320            2325

Ala Ser Ser Glu Ala Lys Asp Lys Met Thr Ser Thr Asn Val Ser
    2330                2335            2340

Gln Lys Asp Asp Thr Ala Thr Ala Asp Thr Asn Asp Thr Gln Lys
    2345                2350            2355

Ser Val Gly Pro Val Ala Asn Asn Lys Ala Lys Asp Met Gln Thr
    2360                2365            2370

Asn Asp Thr Gln Lys Ser Val Gly Ser Ala Ala Asn Asn Lys Ala
    2375                2380            2385

Thr Gln Asn Asp Gly Ala Asn Ala Ser Pro Ala Thr Val Ser Asn
    2390                2395            2400

Gly Ser His Ser Met His Gln Asp Met Leu Asn Val Thr Lys Pro
    2405                2410            2415

Glu Glu Asn Lys Ala Asn Ala Lys Ser Asp Gln Gln Gly Lys Val
    2420                2425            2430

Asn Lys Pro Lys Gln Gln Ala Lys Thr Leu Pro Asp Thr Gly Met
    2435                2440            2445

Ser His Asn Asp Asp Leu Pro Tyr Ala Glu Leu Ala Leu Gly Ala
    2450                2455            2460

Gly Met Ala Phe Leu Ile Arg Arg Phe Thr Lys Lys Asp Gln Gln
    2465                2470            2475

Thr Glu Glu
    2480
```